(12) United States Patent
Turner

(10) Patent No.: US 8,629,181 B2
(45) Date of Patent: Jan. 14, 2014

(54) BIOLOGICALLY ACTIVE OILS

(71) Applicant: Athol Gillies Turner, New South Wales (AU)

(72) Inventor: Athol Gillies Turner, New South Wales (AU)

(*) Notice: Subject to any disclaimer, the term of this patent is extended or adjusted under 35 U.S.C. 154(b) by 0 days.

(21) Appl. No.: 13/671,401

(22) Filed: Nov. 7, 2012

(65) Prior Publication Data

US 2013/0064808 A1    Mar. 14, 2013

Related U.S. Application Data

(60) Division of application No. 13/232,408, filed on Sep. 14, 2011, now Pat. No. 8,329,748, which is a division of application No. 12/125,024, filed on May 21, 2008, now Pat. No. 8,039,512, which is a continuation of application No. 10/559,599, filed as application No. PCT/AU2004/000745 on Jun. 4, 2004, now abandoned.

(30) Foreign Application Priority Data

Jun. 4, 2003  (AU) ................. 2003902823

(51) Int. Cl.
*A61K 31/20* (2006.01)
*C12P 7/64* (2006.01)

(52) U.S. Cl.
USPC .......................................... 514/558; 435/134

(58) Field of Classification Search
None
See application file for complete search history.

(56) References Cited

U.S. PATENT DOCUMENTS

| | | | |
|---|---|---|---|
| 4,485,173 A | 11/1984 | Gierhart | |
| 5,374,657 A | 12/1994 | Kyle | |
| 5,431,924 A | 7/1995 | Ghosh et al. | |
| 5,834,027 A | 11/1998 | Cardinale Fezler | |
| 2002/0137796 A1* | 9/2002 | Schade et al. ............ | 514/558 |

FOREIGN PATENT DOCUMENTS

| | | |
|---|---|---|
| EP | 0 117 087 B1 | 6/1987 |
| GB | 2293547 A | 4/1996 |
| JP | 64-051091 | 2/1989 |
| JP | 03-206891 | 9/1991 |
| JP | 06-253786 | 9/1994 |
| JP | 08-168390 | 7/1996 |
| JP | 11-221049 | 8/1999 |
| WO | WO 92/08470 A1 | 5/1992 |
| WO | WO 96/34596 A2 | 11/1996 |
| WO | WO 03/075003 A1 | 9/2003 |

OTHER PUBLICATIONS

Stredansky et al, gamma-Linolenic acid production with *Thamnidium elegans* by solid-state fermentation on apple pomace, Bioresource technology, May 2000. vol. 73, No. 1. p. 41-45.*
Bednarski, W., et al., "Growth of Three Fungi on Poultry Fat or Beef Tallow," *World Journal of Microbiology and Biotechnology*, 1993, pp. 656-659, vol. 9(6).
Davies, Rep.—*N.Z. Dep. Sci. Ind. Res. Ind. Process. Div.*, 1983, IPDTSO/2011, pp. 56.
Floetenmeyer, M.D., et al., "Continuous culture Fermentation of Whey Permeate to Produce Microbial Oil," *J Dairy Sci*, 1985, pp. 633-637, vol. 68.
Gandhi, N.N., "Applications of Lipase," *JAOCS*, 1997, pp. 621-634, vol. 74 (6).
Ghosh, P.K., et al., "Microbial Lipases: Production and Applications," *Science Progress*, 1996, pp. 119-157, vol. 79 (2).
Hamm, W., "Liquid-Liquid Extraction in the Food Industry," in *Handbook of Solvent Extraction*, 1983, pp. 593-595 (New York, John Wiley & Sons).
Kakio, et al., Chemical and Microbiological Characteristics of Sardine Meal Fermented With *Aspergillus oryzae* IFO 4202, *Food Science and Technology International*, 1997, pp. 61-68, vol. 3(1).
Lazar, G. and Schroder, F.R., "Degradation of Lipids by Fungi," *Microbial Degradation of Natural Products*, 1992, pp. 267-291, VCH Publishers, Inc., New York.
Magan, N., et al., "Lipolytic Activity and Degradation of Rapeseed Oil and Rapeseed by Spoilage Fungi," *International Journal of Food Microbiology*, 1993, pp. 217-227, vol. 19.
Okumura, S., et al., "Synthesis of Various Kinds of Esters by Four Microbial Lipases," *Biochimica et Biophysica Acta*, 1979, pp. 156-165, vol. 575.
Pandey, A., et al., "Review: The Realm of Microbial Lipases in Biotechnology," *Biotechnol. Appl. Biochem.*, 1999, pp. 119-131, vol. 29.
Papanikolaou, S., et al., "Single Cell Oil Production by *Yarrowia Lipolytica* Growing on an Industrial Derivative of Animal Fat in Batch Cultures," *Appl Microbial Biotechnol*, 2002, pp. 308-312, vol. 58.
Steinkraus, K.H., "Solid-State (Solid-Substrate) Food/Beverage Fermentations Involving Fungi," *Acta Biotechnol.*, 1984, pp. 83-88, vol. 4, No. 2.
Stredansky, M., et al., "γ-Linolenic Acid Production with *Thamnidium elegans* by Solid-State Fermentation on Apple Pomace," *Bioresource Technology*, 2000, pp. 41-45, vol. 73.
Whitehouse, M.W.,et al., "Emu Oil(s): A Source of Non-Toxic Transdermal Anti-Inflammatory Agents in Aboriginal Medicine," *Inflammopharmacology*, 1998, pp. 1-8, vol. 6(1).
http://www.cyberlipid.org/extract/ext0001.htm, 2007

* cited by examiner

*Primary Examiner* — Qiuwen Mi

(74) *Attorney, Agent, or Firm* — Alston & Bird LLP

(57) ABSTRACT

A process for the production of fats or oils and their extracts containing biologically active chemical compounds from a lipid substrate, the process comprising: a) inoculation of a lipid substrate with fungally derived lipolytic enzymes; b) incubating the inoculated substrate for a period of between about 7-120 days at a temperature of between about 4-35° C., at a humidity of between about 75-100%, and c) processing said substrate mixture to obtain a biologically active fat or oil.

6 Claims, 20 Drawing Sheets

Figure 3: The 5-Lipoxygenase Pathway of Human Neutrophils
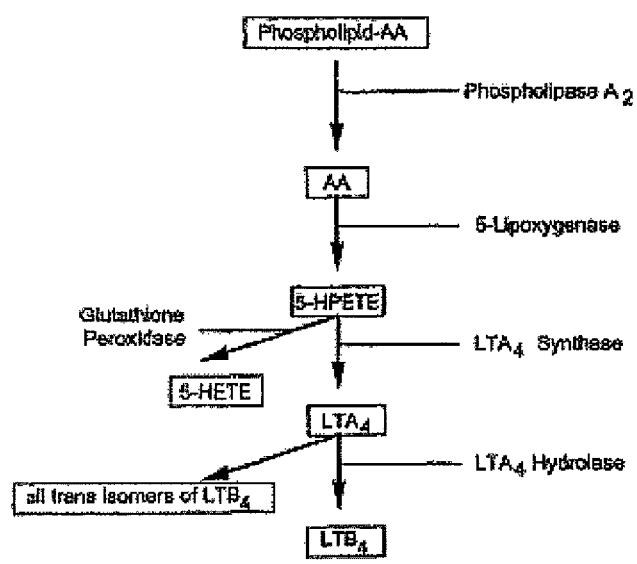

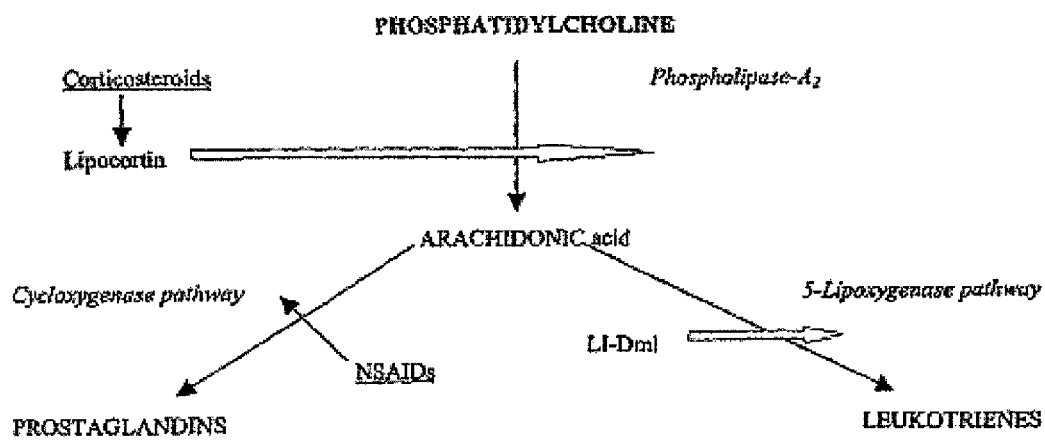
Figure 4: How steroids and the lipoxyegnase inhibitor(s) (LI-Dml) from an active emu oil can act co-operatively to suppress pro-inflammatory leukotrienes.
*(Broad arrows show sites of enzyme inhibition)*

BIOLOGICALLY ACTIVE OILS

CROSS-REFERENCE TO RELATED APPLICATIONS

This application is a divisional of U.S. application Ser. No. 13/232,408, filed Sep. 14, 2011, which was a divisional of U.S. application Ser. No. 12/125,024, now U.S. Pat. No. 8,039,512, filed May 21, 2008, which was a continuation of U.S. application Ser. No. 10/559,599, filed Dec. 2, 2005, now abandoned, which was national stage filing under 35 U.S.C. §371 of PCT/AU2004/000745, filed Jun. 4, 2004, which International Application was published by the International Bureau in English on Dec. 16, 2004, which claims priority to Australian Patent Application AU-2003902823, filed Jun. 4, 2003, each of which is incorporated by reference in its entirety herein.

TECHNICAL FIELD

The present invention relates to fungal metabolism/transformation of lipid substrates to produce fats and more particularly oils and their extracts containing biologically-active chemical compounds for the treatment or prophylaxis of diseases, disorders or conditions in humans and other animals.

BACKGROUND OF THE INVENTION

With the growth of the alternative/complementary medicine industry and the general perception in some areas that the products are "snake oil" remedies, there is a pressing need to ensure that products supplied by this alternative industry have reproducible efficacy and are safe for use by the general public. However, due to recent adverse publicity by the press and government regulators there is an absolute requirement for alternative medicines to meet strict guidelines regarding the quality of the raw materials and the method of manufacture. One of the major difficulties with alternative medicines is that the ingredients used are often composed of materials which in most cases may contain many different chemical compounds. Hence there is an enormous challenge involved to ensure efficacy and safety of the products for use by society. One of the major reasons for the lack of knowledge of the effectiveness of these products is that the alternative and complementary medical industry generally pride themselves on the fact these products are not animal tested, hence their claims cannot be validated.

Historically, the animal and plant oil industries are among the oldest in the world, hence procedures used in this industry are well established. In addition the industrial and medical applications, of which there are many, are well documented in the literature. However, many oils such as olive, evening primrose oil, flaxseed oil, cod liver oil and emu oil are used to treat a variety of medical conditions and diseases but virtually no attention has been paid to the difficulty in reproducing efficacy and safety data for these types of products. In fact, over the past thirteen years of animal and chemical testing of a large variety of many different types and batches of animal and plant oils, large variation in biological activity and chemical composition has been observed.

It has been increasingly recognised in this area that in order to increase the credibility of complementary/alternative medicines based on animal and plant extracts, particularly oils, quality control in terms of reproducibility of efficacy and safety data for these types of products is of foremost concern.

OBJECT OF THE INVENTION

It is therefore an object of the present invention to provide processes for the production of animal and plant-derived oils and their extracts containing biologically-active chemical compounds having therapeutic and prophylactic activity in respect of a wide range of diseases and conditions in humans and other animals.

It is another object of the present invention to provide pharmaceutical compositions formulated for administration by any route, including without limitation, oral, buccal, sublingual, rectal, parenteral, topical, inhalational, injectable and transdermal, preferably oral or topical, including biologically-active oils and/or their extracts (therapeutic oils and extracts thereof) which demonstrate efficacy across a broad spectrum of diseases, disorders or conditions in humans and other animals, together with pharmaceutically acceptable excipients, carriers or adjuvants.

It is also an object of the present invention to provide a method for the treatment or prophylaxis of a wide range of diseases, disorders and conditions in humans and other animals by the administration of biologically-active oils and/or their extracts obtained according to the processes of the present invention.

It is also an object of the present invention to provide a method for the treatment or prophylaxis of a wide range of diseases, disorders and conditions in humans and other animals by the administration of the fatty acid esters and amides of biologically-active oils and/or their extracts.

It is a further object of the present invention to provide the use of biologically-active oils and/or their extracts in the manufacture of pharmaceutical formulations for the treatment or prophylaxis of a wide range of diseases and conditions in humans and other animals.

SUMMARY OF THE INVENTION

This invention is based on the identification of the major factor/s responsible for the variation in quality of plant and animal derived oils, namely the transformation of the lipid substrates by fungi growing in and on the lipid substrate. The lipid substrates used are obtained from animal and bird fat (obtained by cutting/slicing of fat tissue), plant tissue, seeds, nuts etc. appropriately treated (by either cutting, crushing etc). The quality of the fat or oil produced by this solid state process depends on the type and number of fungi, lipid substrate, temperature, humidity and length (time) of incubation prior to rendering, cold pressing, solvent extraction or super-critical fluid extraction. The basis of this invention therefore relates to the controlled use of fungi to transform lipid substrate/s to produce oils which contain biologically-active chemical compounds by the solid state process/s. It has been established by the present inventor that exposure of the lipid substrate to fungi is responsible for the major variation in biological activity (efficacy) of different therapeutic oils rather than temperature, oxygen and light during processing and storage, although these latter factors may have some minor influence.

Accordingly, a first aspect of the present invention provides a process for the production of fats or oils and their extracts containing biologically-active chemical compounds from a lipid substrate, the process comprising:
a) Inoculation of a lipid substrate with a fungal mixture,
b) Incubating the inoculated substrate for a period of between about 7-120 days at a temperature of between about 4-35° C., at a humidity of between about 75-100%, and
c) Processing, said incubated substrate mixture to obtain a biologically active fat or oil.

Fats or oils containing different biologically active chemical compounds may also be produced by simply incubating the prepared animal or plant lipid substrate which is either sliced, ground, minced or chopped and performing steps 2-3 above with careful adjustments to temperature, time and humidity.

A related aspect of the present invention provides a solid state process for the production of oils and their extracts containing biologically-active chemical compounds from a lipid substrate, the process comprising
a) Inoculation of a lipid substrate with a fungal mixture having enzymatic activity, said fungal mixture being derived from said substrate,
b) Incubating the inoculated substrate for a period of between about 7-120 days at a temperature of between about 4-35° C., at a humidity of between about 75-100%, and
c) Processing said substrate mixture to obtain a biologically active fat or oil.

In step b) typically the period of incubation is between about 7 to 56 days at a temperature between about 5-20° C. and at a high humidity of between about 80-100%.

In step c), if the lipid substrate is animal derived, it is typical that the product is a biologically active oil obtained by rendering said inoculated substrate. Alternatively, if said lipid substrate is plant or seed derived, the biologically active oil is obtained by cold pressing, solvent extraction or supercritical fluid extraction of said inoculated substrate mixture.

There is also provided a biologically active product, particularly an oil when produced by the process of the first aspect of the present invention described above.

The typical steps/procedures which must be performed in order to produce the biologically-active oils and fats; assuming we have pure cultures of different strains of fungi in storage are:
1. Inoculation of the sterilised lipid substrate (e.g. animal or plant lipid) with the appropriate fungal mixture;
2. Incubating the above mixture for a specified temperature range, period of time and humidity;
3. Rendering the above mixture;
4. Centrifuging the rendered mixture produced in step 3;
5. Filtering the oil produced from the centrifuge step;
6. Sterilising the oil at 135° C. for two hours;
7. Filtering the oil after sterilising;
8. Storage of the oil;
9. Extraction of the oil if required.

Providing the above procedures are repeated the oil produced will be reproducible within experimental error, as this is a biological process in which some variation will be certain to occur.

The above oils or fats can also be produced by simple preparing the animal or plant lipid source by either slicing, grinding, mincing or chopping and then placing on polymer or stainless steel trays with or without perforations depending on the requirements and then carrying out steps 2-9 above. This step simply involves adjusting the temperature, humidity and time for the metabolism/transformation of the lipid substrate to occur.

Bacteria are not involved in the transformation process. While not wishing to be bound by any theory, it appears that the fungi penetrate the lipid cell walls and secrete enzymes that transform/metabolise the lipid within the cell. Some metabolic products are released from the lipid cell into the medium and while some others are absorbed by the fungi and further transformed internally and either stored there or secreted from the cells.

The fungal mixture used to inoculate the lipid substrate and which is the source of the fungally-derived lipolytic enzymes may be intact/whole fungal organisms, pure fungi, single fungi or mixed fungi, active enzyme extracts thereof, genetically modified organisms or modified enzymes. The process of the present invention transforms the lipids substrate, to fats or oils containing biologically-active chemical compounds which are suitable for treating a wide range of human and veterinary diseases. It is noted that using this method of producing oils and their extracts the amount of free fatty acids, mono and diglycerides are enriched. For example the level of total free fatty acids in some animal and plant oils is increased to or exceeds 14%. The compounds found in the oils and their extracts act synergistically to give the desired biochemical action in humans and animals for the treatment of a wide range of diseases and conditions.

Typically, the lipid substrate can be selected from animal or plant sources, of either terrestrial or marine origin, or the substrate can be constituted from lipids or their extracts impregnated onto artificial substrates supplemented with mineral and organic amendments (see Waller et al 2002, Plant Pathologists Pocketbook 3rd Edition, CABI, New York). Sources of animal lipids include goanna, sheep, chicken, emu, ostrich, camel, duck, geese, pig, cattle, horse, mutton bird, sea cucumber, fish and shellfish including mussels. Sources of plant oils include seeds/nuts of macadamia sp, *Canarium* spp, peanut, sunflower, safflower, linseed, soybean, wheat, oats, barley, almond, avocado, cashew, quandong, maize, wattle, olive, palm and rice. Other vegetable/plant/seed sources include coconut, pili nut, ngali nut, tamanu nut, neem seed, sesame and canola.

Typically, the fungi inoculated onto the lipid substrate will have been isolated from the substrate (i.e. is endogenous to the lipid substrate) and found to transform the specific or similar substrates found within the host lipid substrate. Such fungi are typically found in the sexual and asexual states of the Phyla Zygomycotina, Ascomycotina and Basidiomycotina. This is therefore understood to cover the fungi Deuteromycetes which is the asexual state of the main phyla. Fungi also typically found to transform lipid substrates include *Phoma* sp, *Cladosporium* sp, *Rhodotorula mucilaginosa*, *Cryptococcus albidus*, *Trichosporon pullulans*, *Mucor* spp, *Epicoccom purpurescens*, *Rhizopus stolonifer*, *Penicillium chrysogenum*, *Nigrospora sphaerica*, *Chaetomium globosum*. Fungi demonstrating the ability to transform or having this potential may be typically improved by either traditional or molecular genetic techniques to alter the fungi genotype.

The substrate may also or instead be inoculated with enzymes derived from fungi. Typically these enzymes are endogenous to the fungi, but can also be developed from alternative sources or genetically modified isolates. Such enzymes may also be purified and their activity increased by alteration of their structure using physical, chemical, molecular or other techniques.

Typically, the lipid substrate is sterilised and then inoculated with one or more fungi or their enzymes as required. The substrate may be sliced, minced, chopped or ground to enable it to be spread in a layer typically between 0.5 and 10 cm on a surface that may be a stainless steel tray, or with the base perforated to allow oxygen to the lower surface and oil to drip from the substrate and be collected in a suitable container or an equivalent system. Inoculation uses standard procedures (see Waller et al 2002) including spraying or painting the lipid surface with fungal spores suspended in sterile water. The substrate is then typically incubated for a period between about 7 days and about 120 days, more typically between about 7 and 63 days, or about 7 and 56 days, or about 7 and 42 days, or about 7 and 35 days. Even more typically, the substrate is incubated for a period between about 7 and 28 days or about 7 and 21 days and most typically between 14, 21, 28, 35, 42, 56, and 63 days. The inoculated lipid substrate is incubated at a temperature between 4-35° C., typically around 5-20° C., and a relative humidity between 80-100%, typically 95%.

Following incubation the animal lipid substrate including the transformed or metabolised substrate, containing the fungi is minced or ground and transferred to a stainless vessel prior to the rendering process. This process typically involves rendering at a temperature between 40-80° C., typically around 70-75° C. with constant slow speed stirring until the lipid substrate has melted into oil. This oil is then typically centrifuged and filtered and can be further extracted. The filtrate which contains the biologically active oil is then typically further sterilised by heating for a period of between about 15 minutes and about 8 hours, more typically between about 1 hour and 6 hours, even more typically between about 1 hour and 4 hours. Typically the filtrate is heated to a temperature between about 100-160° C., more typically between about 110-150° C. and even more typically between about 120-140° C., most typically about 130-135° C.

In the case of plant seed, nut oils or other lipid sources not of animal origin, the inoculated and incubated lipid substrate/s containing fungi may be minced or ground prior to cold pressing using a screw press, the oil from the screw press then being centrifuged and filtered. This oil is then typically sterilised by heating for a period of between about 15 minutes and about 8 hours, more typically between about 1 hour and 6 hours, even more typically between about 1 hour and 4 hours. Typically the oil is heated to a temperature between about 100-160° C., more typically between about 110-150° C. and even more typically between about 120-140° C., most typically about 130-135° C. The oil produced is then treated as for animal substrates.

The oil obtained from the above processes may then be subjected to solvent extraction which typically involves mixing the oil on a mass or volume basis in the ratio of 1:1 or 2:1 solvent to oil then cooling at a temperature of between 20° C. to −40° C. for a time period from 30 minutes up to 24 hours, typically 0° C. for 16 hours. The solvent is decanted or poured off, centrifuged if required containing, and evaporated dryness to obtain the extract. The resulting residue contains the biologically-active chemical compounds.

The oil or extracts from the above processes may also be subjected (including any derivatives obtained by chemical treatment of oils and their extracts) to the following processes in order to obtain specific fractions or chemical compounds,
(1) High performance liquid chromatography, experimental conditions used will depend on the chemical and physical properties of chemical compounds required for treatment of specific human and animal diseases and conditions.
(2) Super fluid chromatography, experimental conditions used will depend on the chemical and physical properties of chemical compounds required for treatment of specific human and animal diseases and conditions.
(3) Wiped-Film Molecular Still or Evaporator (e.g. Pope), experimental conditions used will depend on the chemical and physical properties of chemical compounds required for treatment of specific human and animal diseases and conditions.
(4) Hybrid Still incorporating Wiped-Film Evaporator and Fractional Distillation Column.
(5) Molecular Distillation Plant or any combination of the above items in (3), (4) and (5), experimental conditions used will depend on the chemical and physical properties of chemical compounds required for treatment of specific human and animal diseases and conditions.

A second aspect of the present invention provides a method for the treatment or prophylaxis of a wide range of diseases, disorders and conditions in humans and other animals by the administration of the fatty acid esters and/or amides of biologically-active oils and/or their extracts (therapeutic oils and extracts thereof). Esters include methyl, ethyl, propyl and isopropyl groups. Methyl and isopropyl esters of the extracts of these oils have been in-vivo tested successfully on rats for the treatment of arthritis with success.

A related aspect of the present invention provides the use of the fatty acid esters and/or amides of biologically-active oils produced according to the present invention, and/or their extracts, for the preparation of a medicament for the treatment or prophylaxis of a wide range of diseases, disorders and conditions in humans and other animals by the administration.

Typically, the biologically active oils and their extracts (therapeutic oils and extracts thereof) produced can be used to treat and/or prevent a wide range of diseases, disorders or conditions in humans and other animals. Typical diseases, disorders or conditions which may be treated or prevented include: respiratory diseases or conditions such as asthma, bronchial disease and chronic obstructive pulmonary disease (COPD), vascular diseases or conditions such as atherosclerosis, coronary artery diseases, hypertension and sickle cell disease-associated vaso-occlusion, skin diseases or conditions such as various dermatitis, psoriasis and atopic eczema, all types of burns, gastrointestinal diseases or conditions such as ulcers, gastric reflux, inflammatory bowel disease, ulcerative colitis, Crohn's disease, pancreatitis and periodontal disease, cancers including bowel cancer and prostate cancer, sarcoidosis, septic shock, musculo-skeletal diseases or conditions such as arthritis including osteoarthritis and rheumatoid arthritis, chronic joint and ligament pain, leukemia, diabetes, allergy including otitis media and ocular allergy, uveitis, dysmenorrhoea, kidney diseases or conditions including glomerulonephritis and nephritic syndrome and prostate diseases or conditions such as benign prostate hyperplasia, and a wide variety of inflammatory disorders. The biologically active oils produced can also increase bone mass density and improve bone strength and connective tissue disorders.

The biologically active oils and their extracts (therapeutic oils and extracts thereof) appear to reduce the levels of C reactive protein (CRP) in the blood of animals and humans (Refer to test results for patient 7 in the examples of therapeutic activity below). Hence these oils and their extracts may used to treat a wide range of human and animal diseases and conditions associated with an elevation of CRP.

CRP belongs to the pentraxin family of proteins, so-called because it has five identical subunits, encoded by a single gene on chromosome 1, which associate to form a stable disc-like pentameric structure. It was so named because it reacts with the somatic C polysaccharide of Streptococcus pneumoniae, and was first discovered in 1930 by Tillet and Frances. In the presence of calcium, CRP specifically binds to phosphocholine moieties. This gives CRP a host-defensive role, as phosphocholine is found in microbial polysaccharides (where CRP-binding activates the classical complement pathway and opsonises ligands for phagocytosis), in platelet-activating factor (PAF) (which is neutralised), and in polymorphs (causing down-regulation).

CRP is exclusively made in the liver and is secreted in increased amounts within 6 hours of an acute inflammatory stimulus. The plasma level can double at least every 8 hours, reaching a peak after about 50 hours. After effective treatment or removal of the inflammatory stimulus, levels can fall almost as rapidly, as CRP has a plasma half-life oft the 5-7- hours. Some of the most common conditions associated with major elevations of CRP levels are:

(a) Inflammatory diseases such as various forms of arthritis including rheumatoid arthritis, psoriatic arthritis and juvenile chronic arthritis, Crohn's disease, ulcerative colitis, Reiter's disease etc.
(b) Malignancies such as lymphoma, sarcoma.
(c) Necrosis such as myocardial infarction, tumour embolisation and acute pancreatitis.
(d) Trauma such as burns and fractures.
(e) Rheumatic fever, tuberculosis, allograft rejection and leukemia.

In addition, the biologically active oils and their extracts (therapeutic oils and extracts thereof) inhibit the secretion of prostaglandin $PGE_2$ from the mouse fibroblast cell line (see Table 9 which summarises the Percent Inhibition of Secreted $PGE_2$ from 3T3 cells exposed to Oil Extracts). This data demonstrates that these oils and their extracts appear to inhibit the cyclooxygenase pathways. Hence these oils and their extracts can be used to treat a wide range of human and animal diseases and condition associated with increases in the COX pathway activity. These types of inhibitors may be used to treat diseases and conditions in humans and animals such as rheumatoid arthritis, osteoarthritis, pain, etc.

The biologically active extracts inhibit leukotriene synthesis by inhibition of the lipoxygenase pathways (including the 5-, 12- and 15—LOX pathways.

The biologically active oils produced have also been noted to synergistically enhance the efficacy of a variety of pharmaceuticals including the corticosteroids, dexamethasone and prednisolone. Such synergy is of great clinical benefit as raised levels of pro-inflammatory leukotrienes or 5-lipoxygenase are associated not only with asthma but also with rheumatoid arthritis, osteoarthritis, scleroderma and inflammatory bowel diseases such as Crohn's disease, and the administration of an active oil of the present invention allows lower doses of steroids to be used. (See FIG. 4 for the synergistic action of a lipoxygenase inhibitor plus a steroid.)

A third aspect of the present invention provides a pharmaceutical composition comprising a biologically active oil, or a fatty acid ester and/or amide of a biologically-active oil and/or an extract thereof, together with a pharmaceutically acceptable carrier, excipient or adjuvant. Typically, the compositions can be in the form of immediate release, extended release, pulse release, variable release, controlled release, timed release, sustained release, delayed release, long acting, and combinations thereof.

BRIEF DESCRIPTION OF THE DRAWINGS

A preferred form of the present invention will now be described by way of example with reference to the accompanying drawings wherein:

FIG. 3 is a summary of the enzymatic pathways acted upon by the biologically active oils to suppress pro-inflammatory leukotrienes FIG. 4 shows how steroids and the lipoxygenase inhibitor(s)(LI) from a biologically-active emu oil (therapeutic oils) can act co-operatively to suppress pro-inflammatory leukotrienes.

DETAILED DESCRIPTION OF THE PREFERRED EMBODIMENTS

Figure 1:
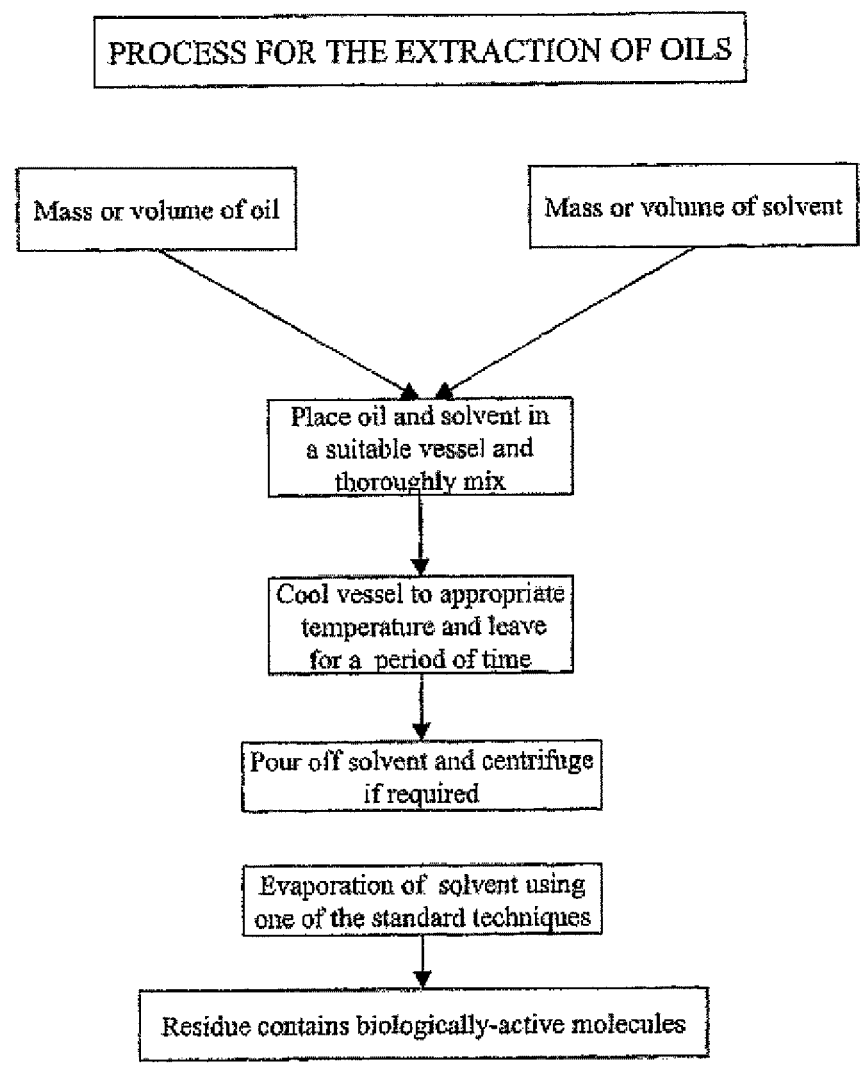
FIG. 1 is a flow chart of the process for extraction of biologically active oils from the crude oil/filtrate.
Figure 2:
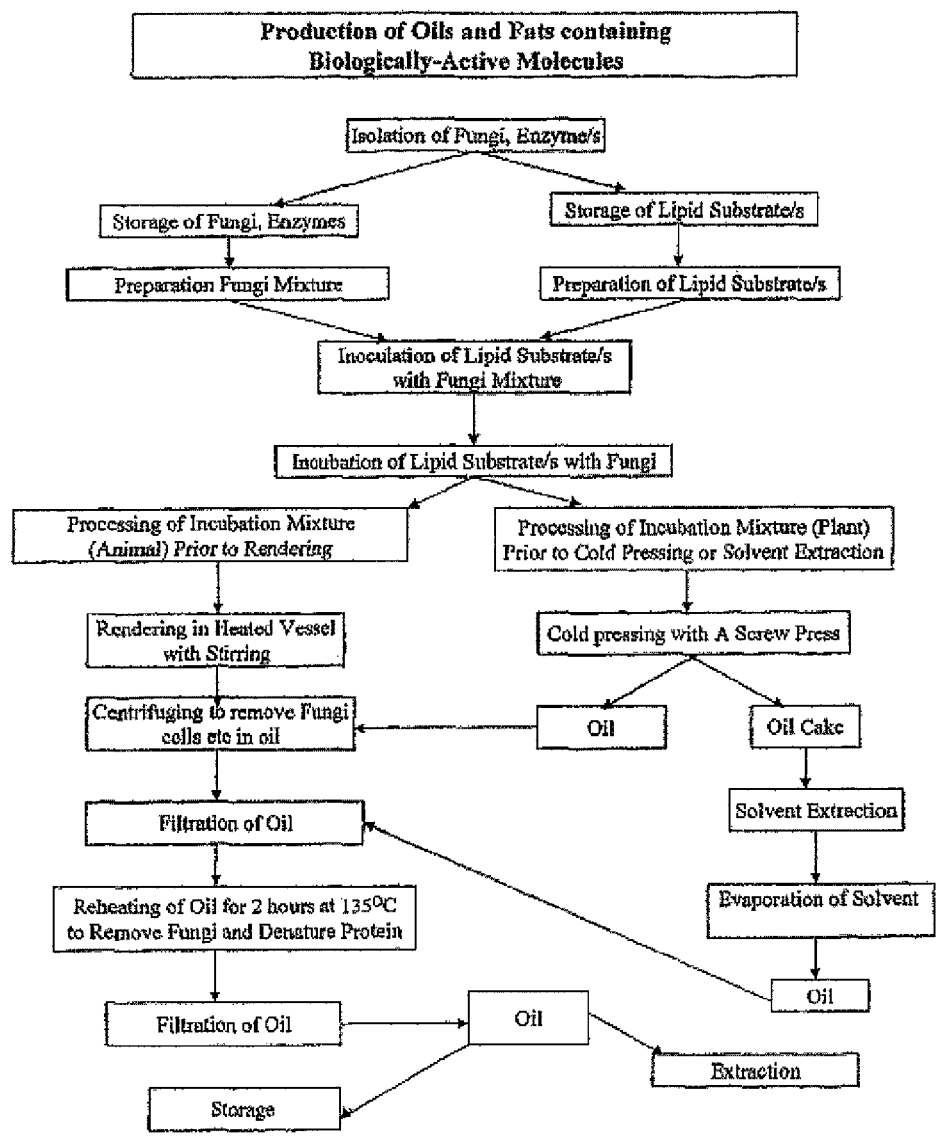
FIG. 2 is a flow chart of the process for production of biologically active oils according to the present invention.
Figure 5A:
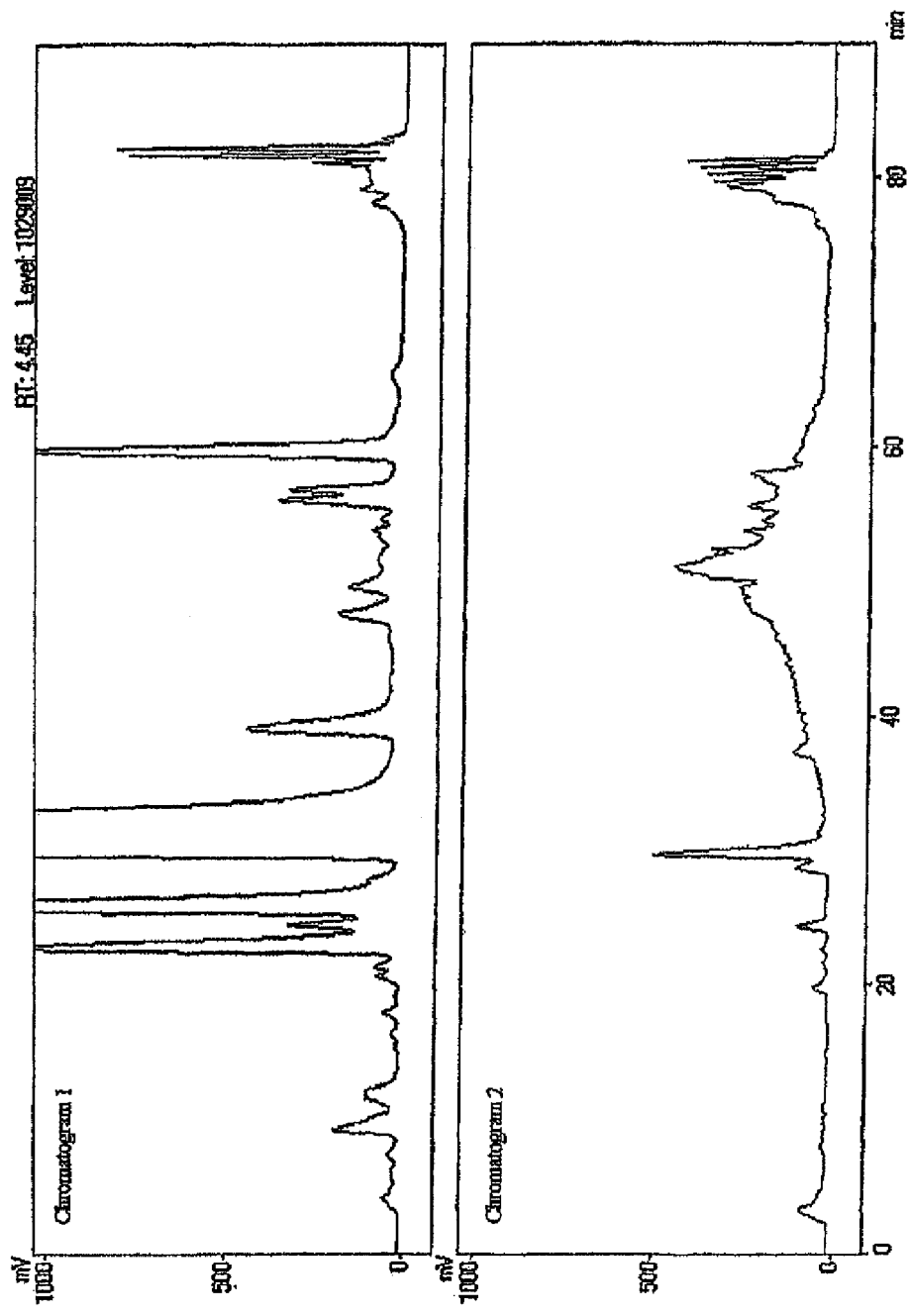
FIGS. 5A-P show chromatograms, numbered 1 to 32, which reflect the biological activity of each sample in Tables 1 to 8, as summarized in Table 11.
Figure 5B:
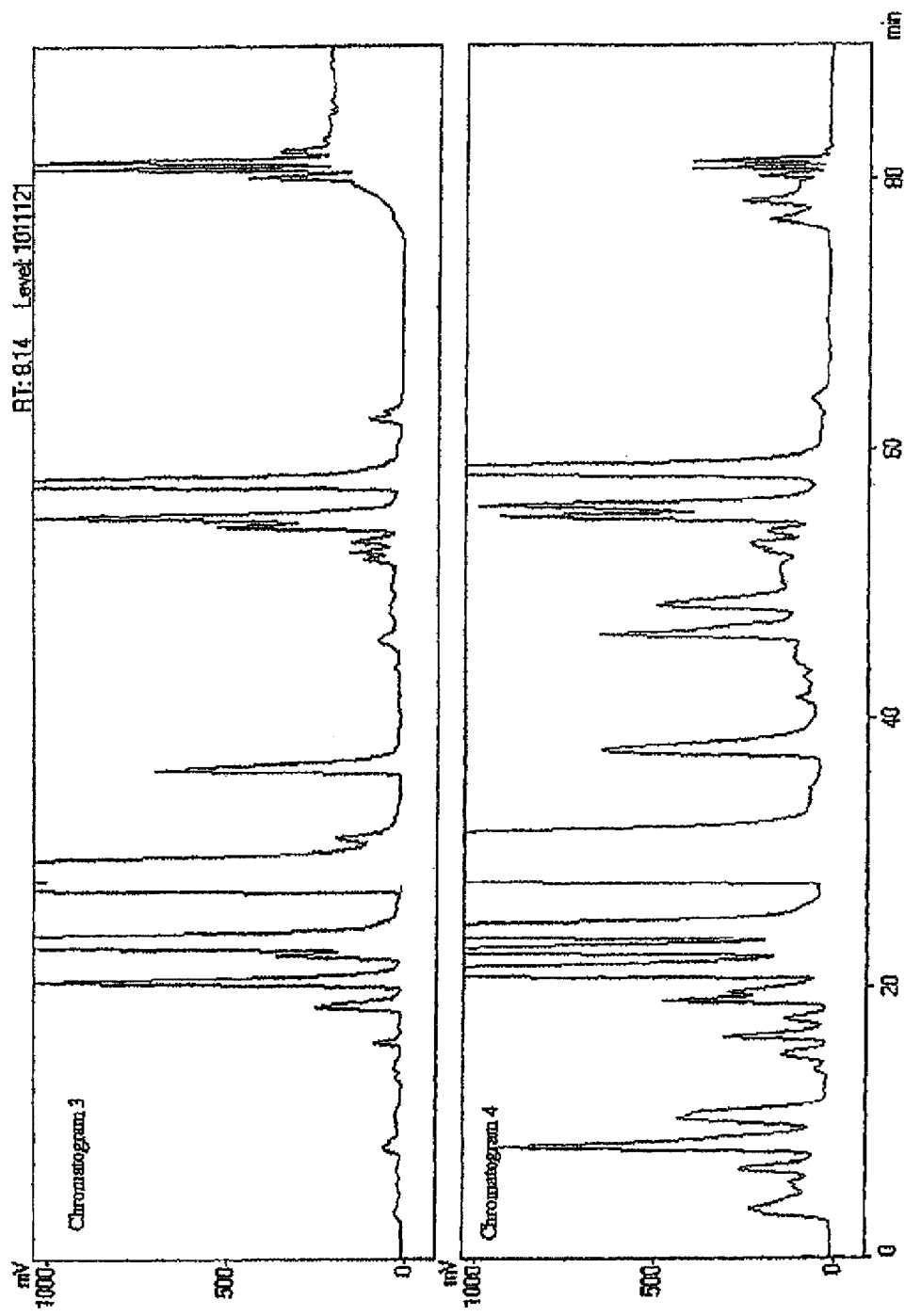
Figure 5C:
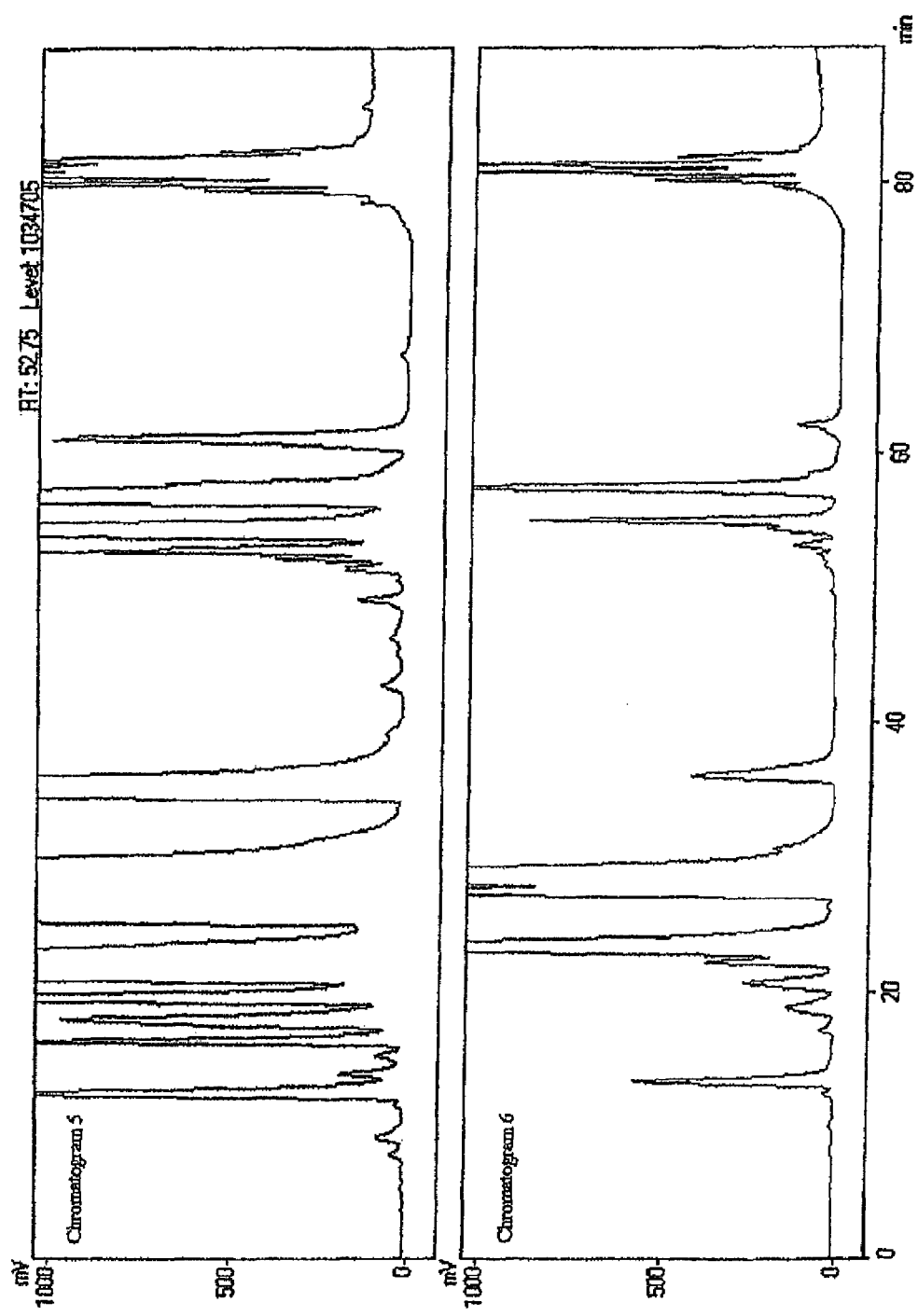
Figure 5D:
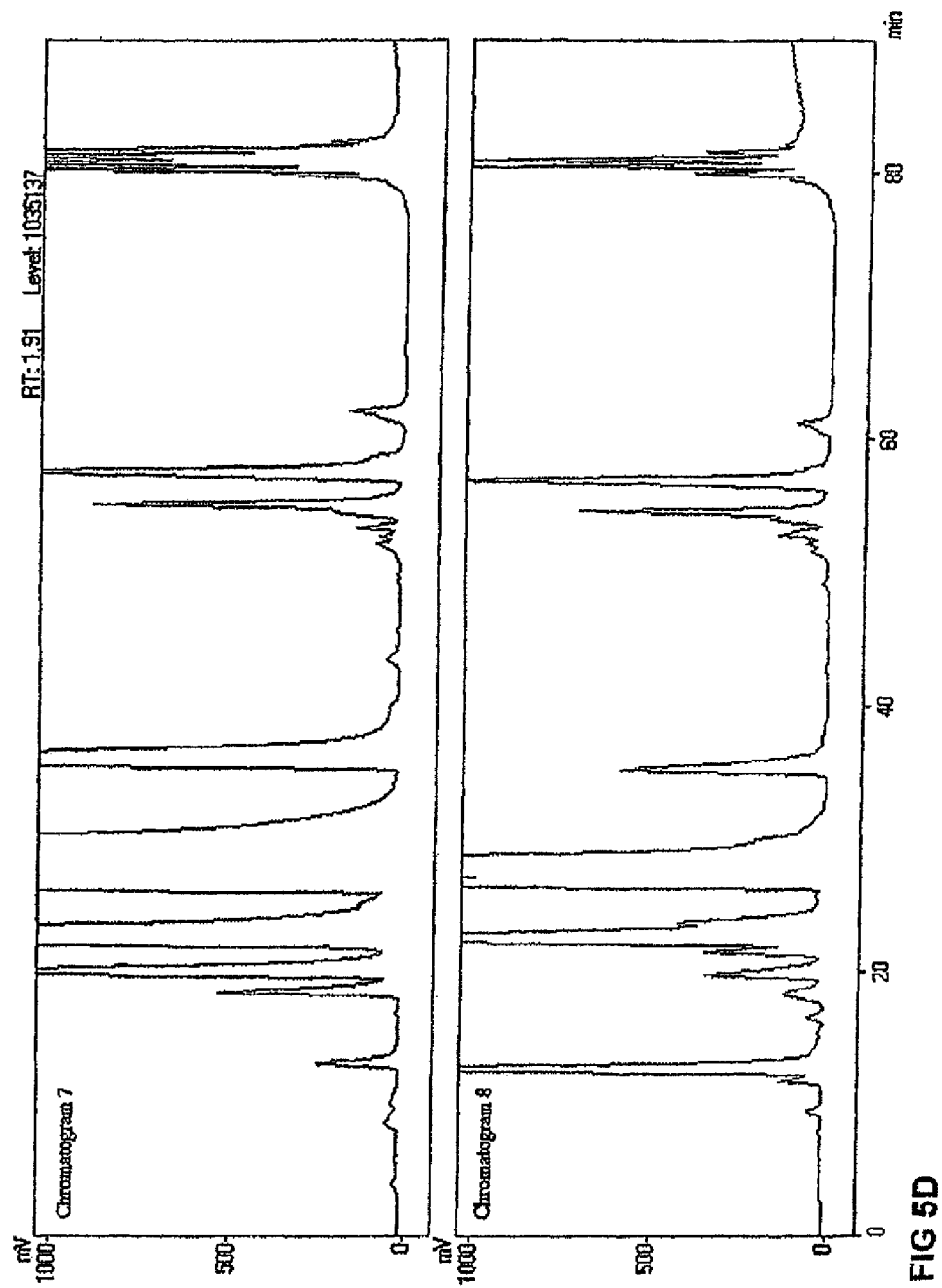
Figure 5E:
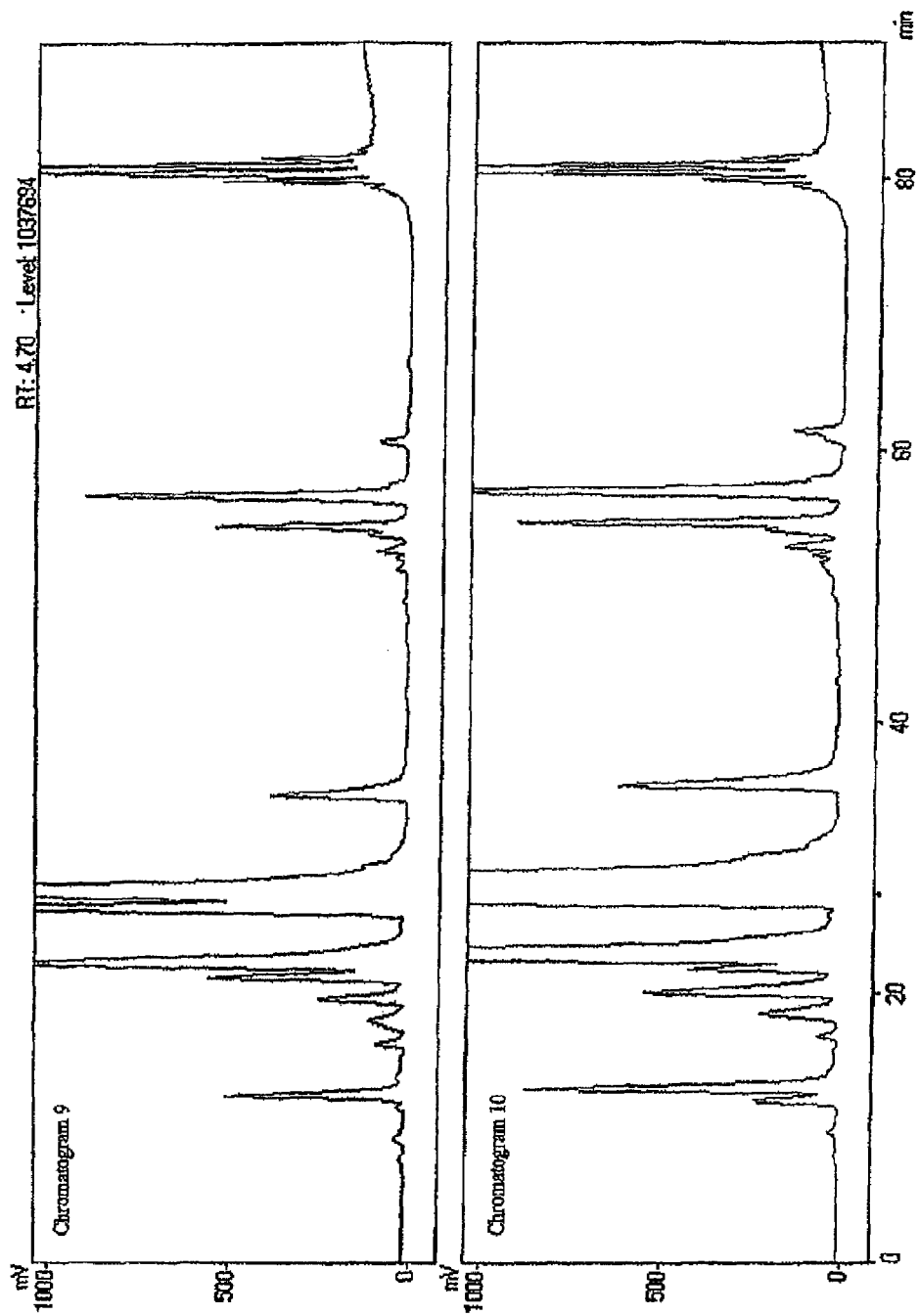
Figure 5F:
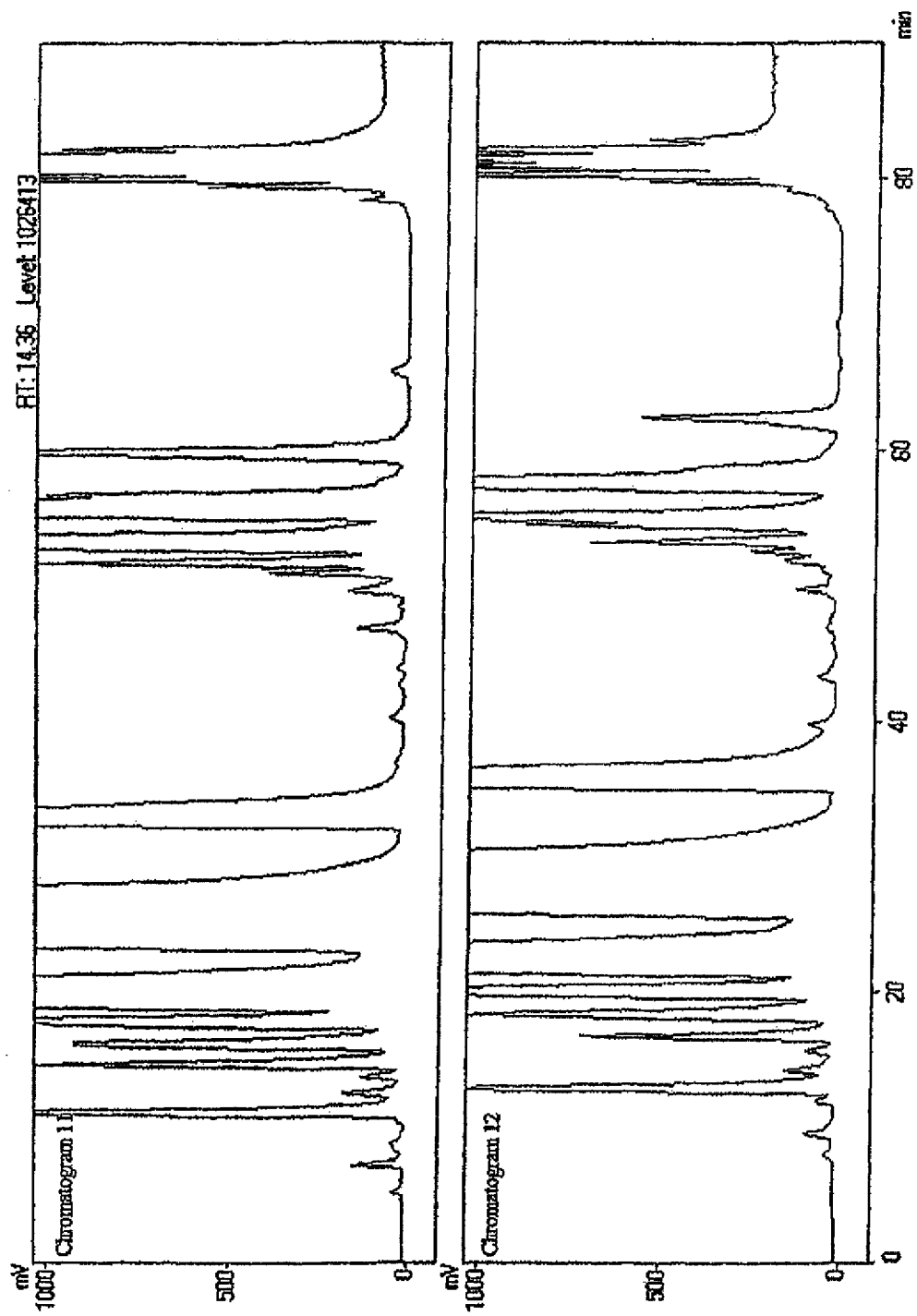
Figure 5G:
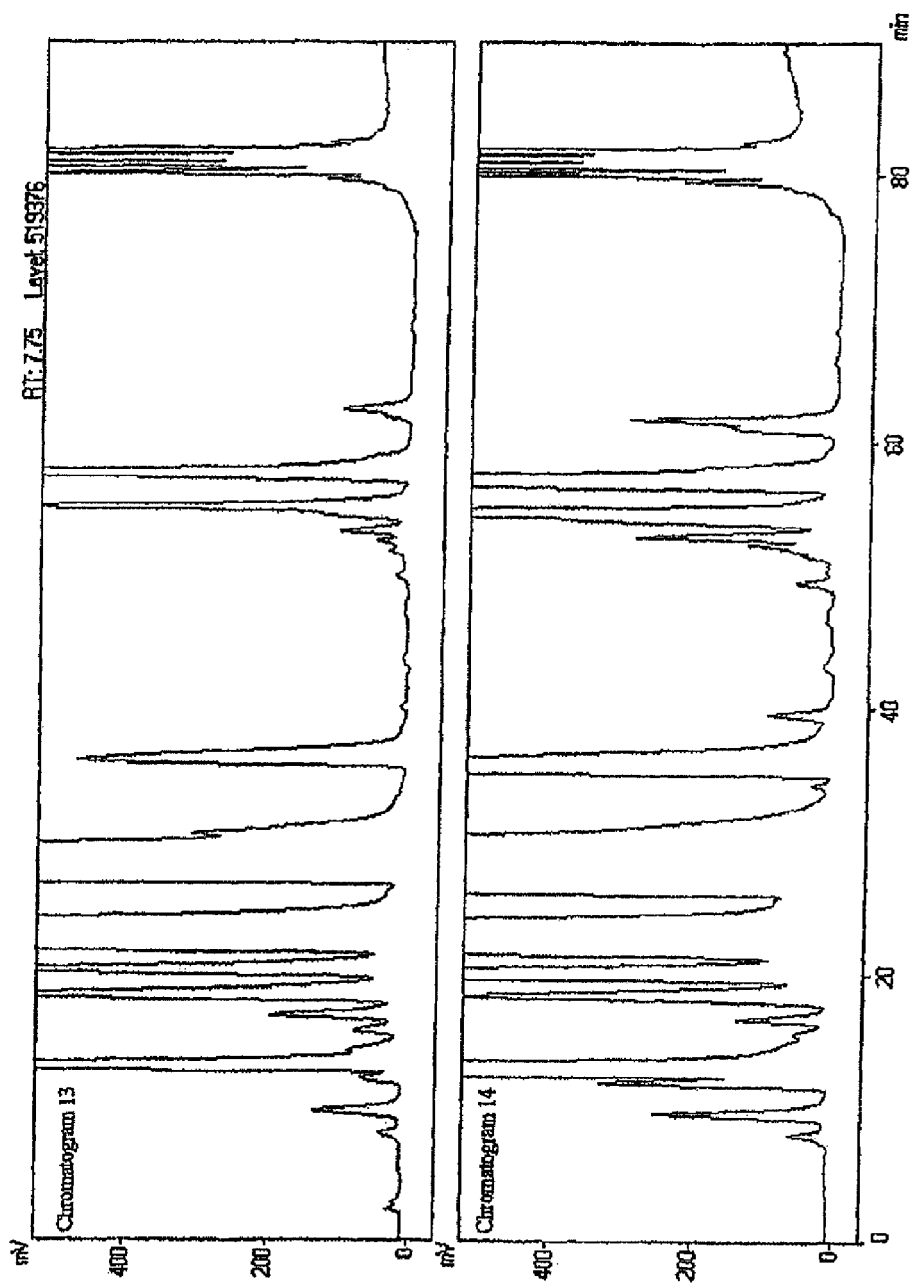
Figure 5H:
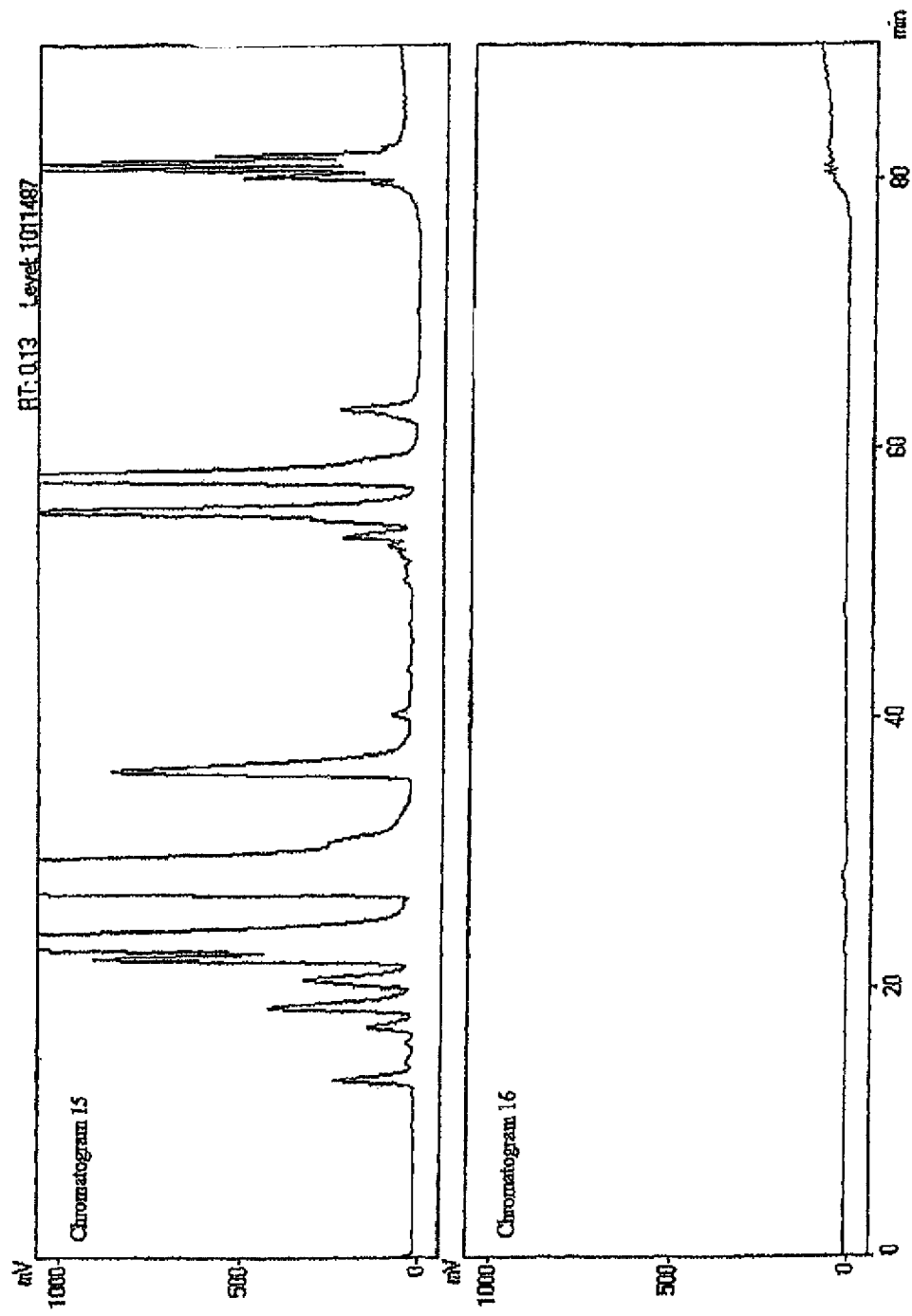
Figure 5I:
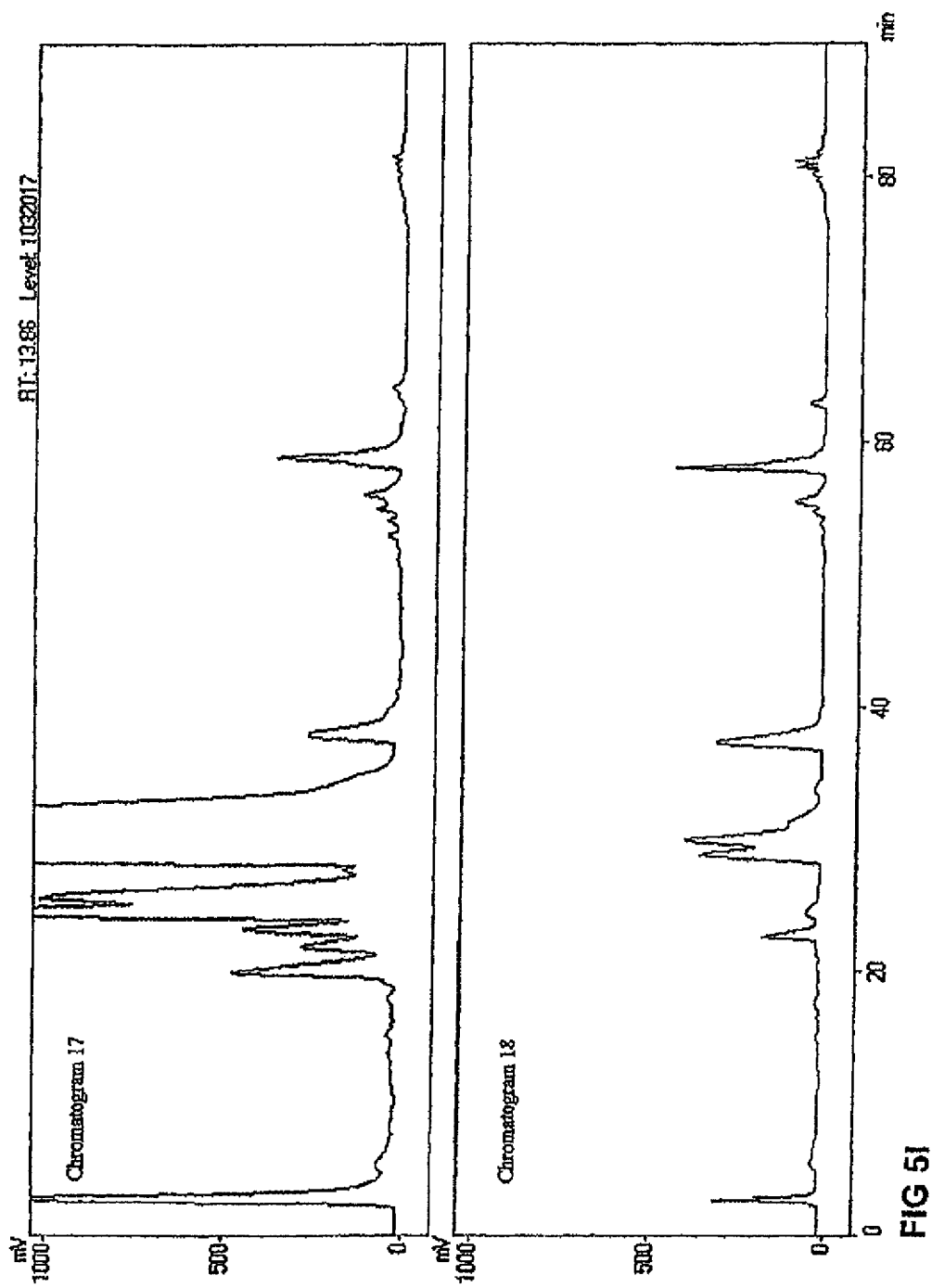
Figure 5J:
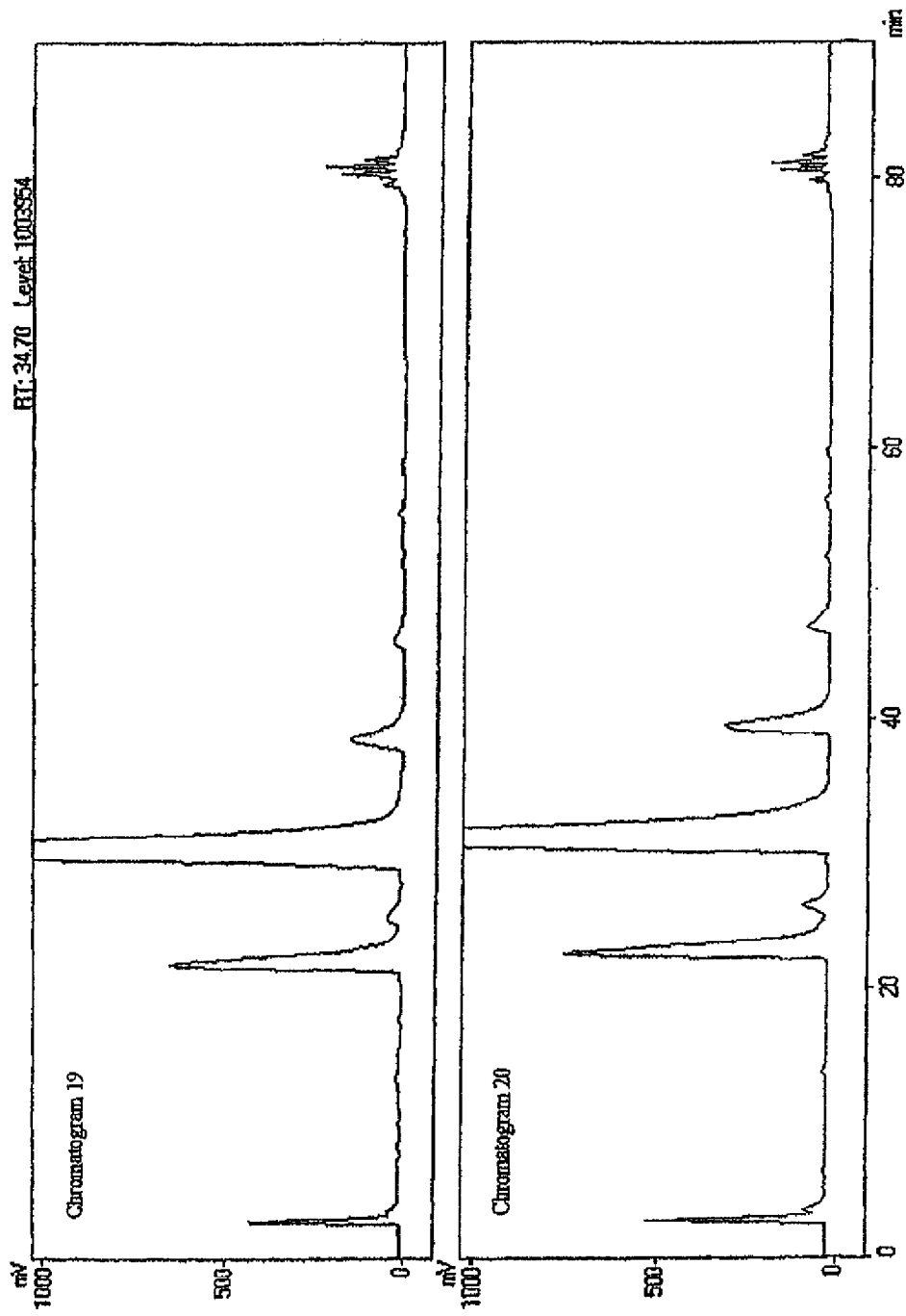
Figure 5K:
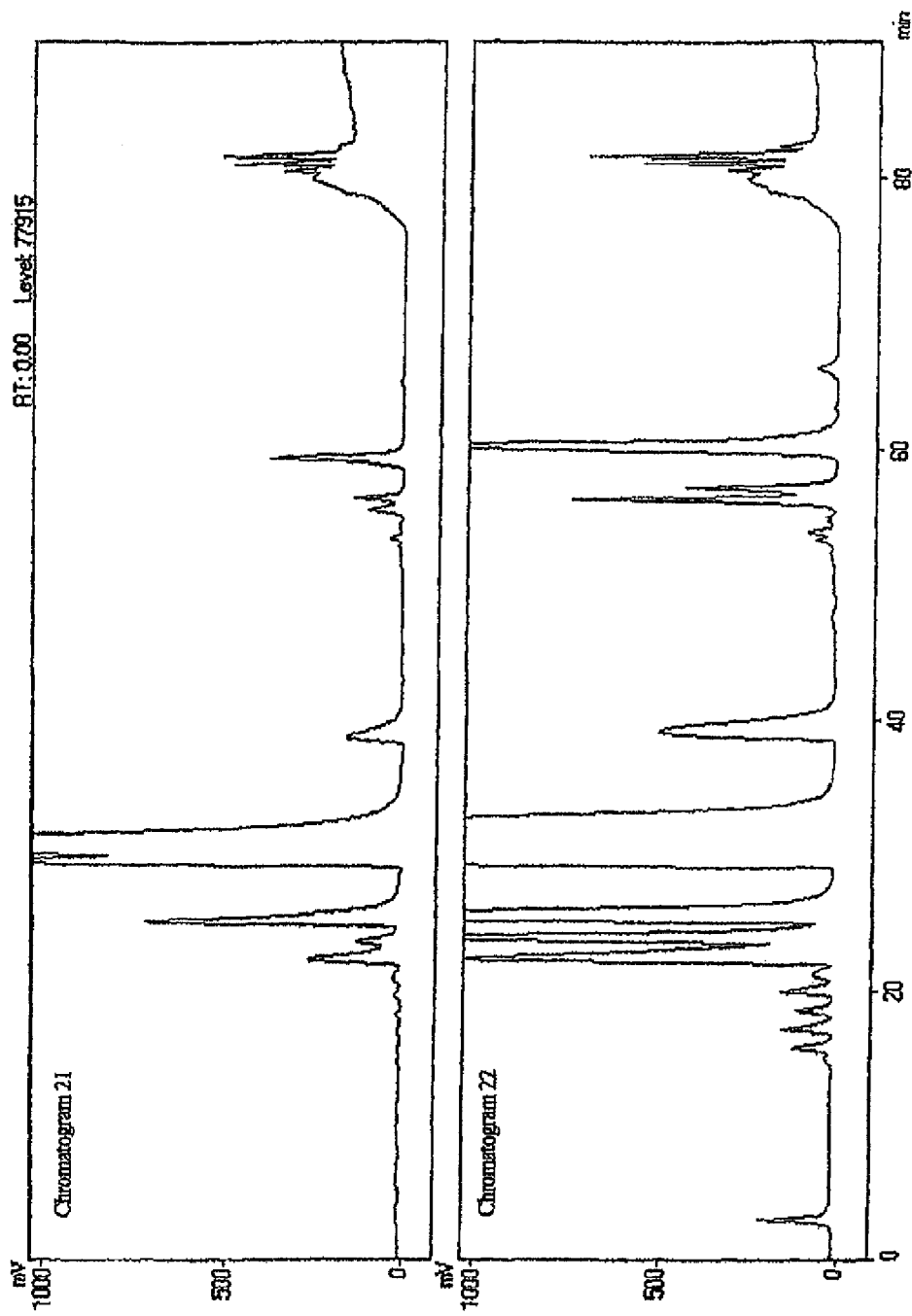
Figure 5L:
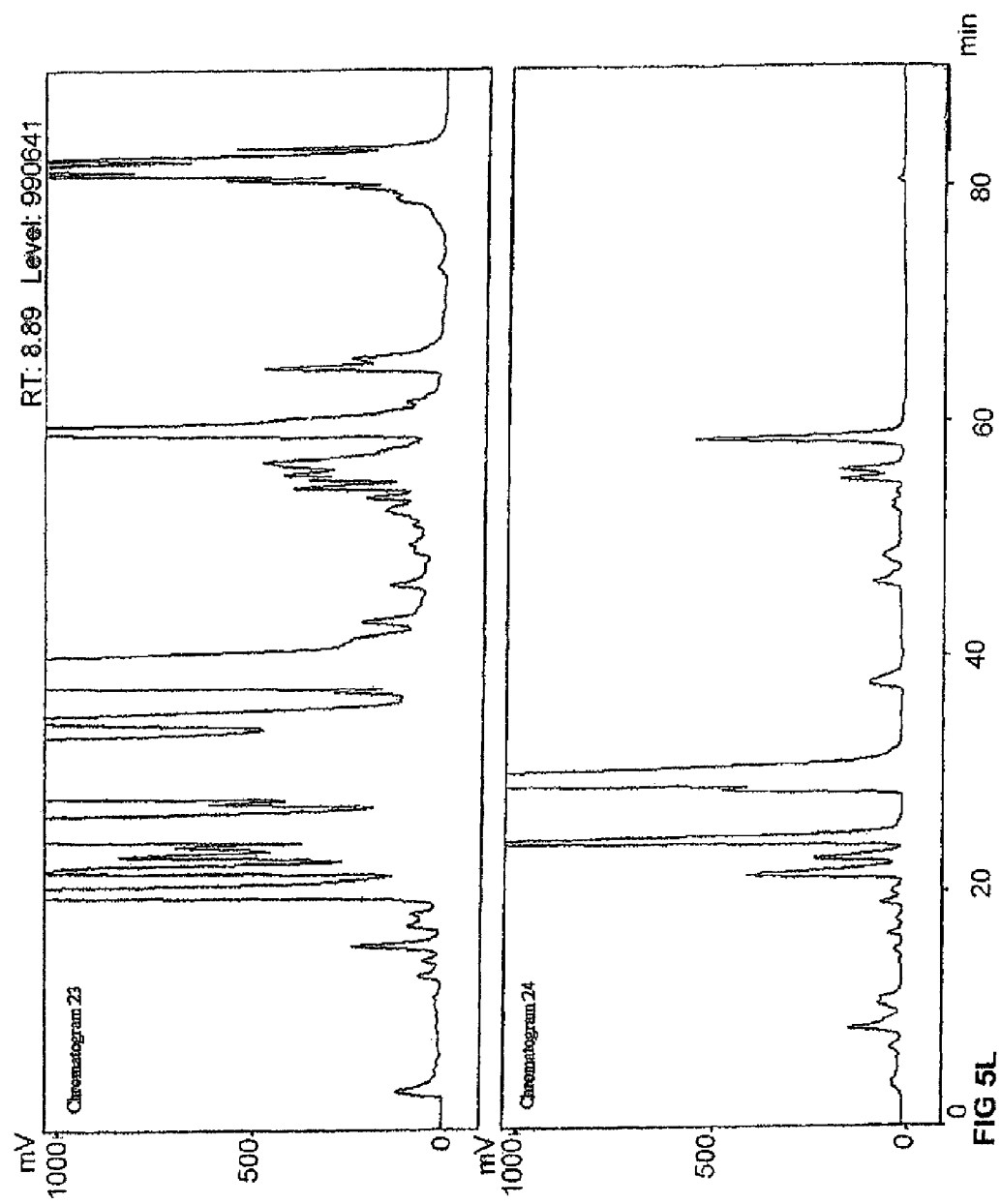
Figure 5M:
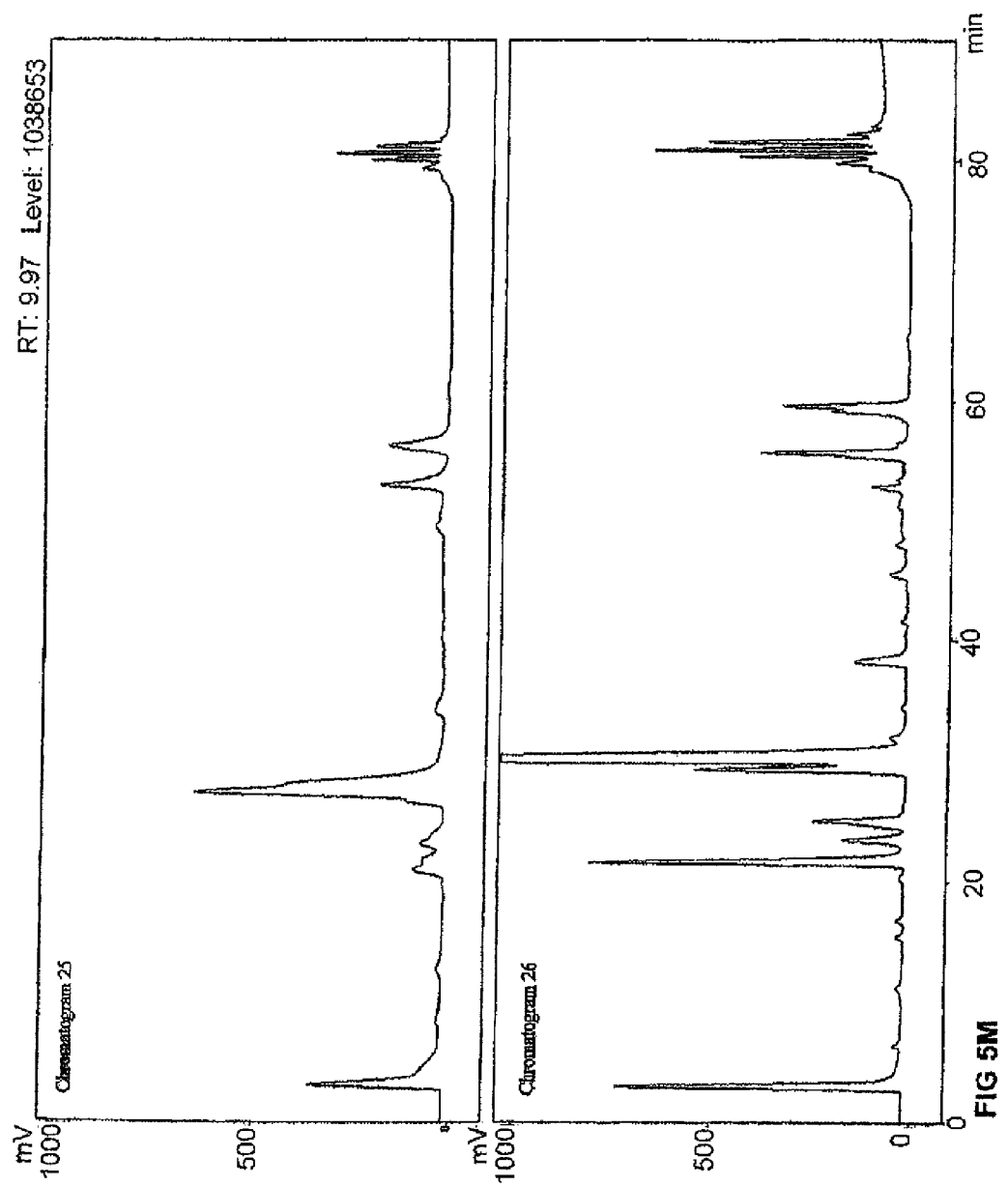
Figure 5N:
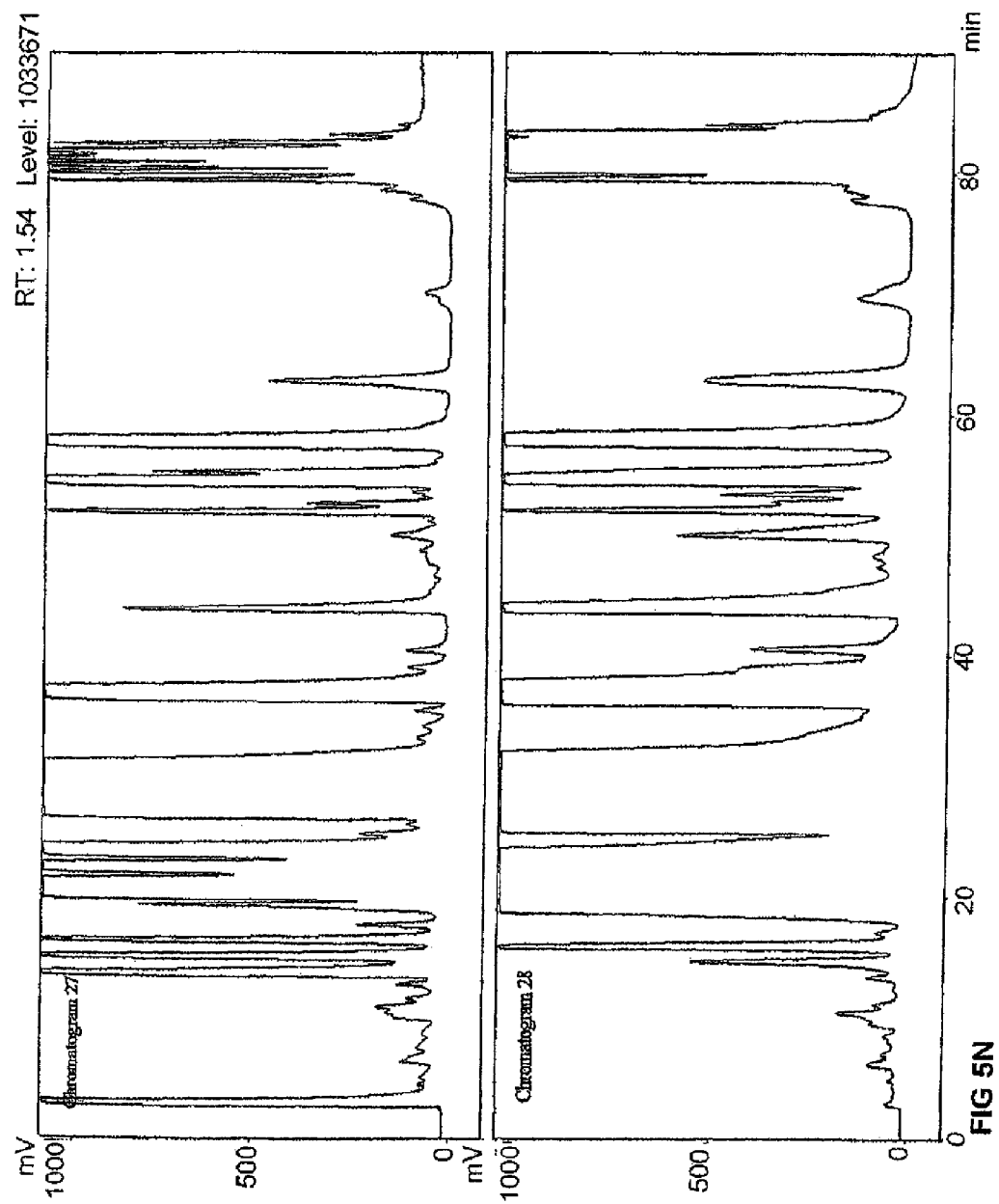
Figure 50:
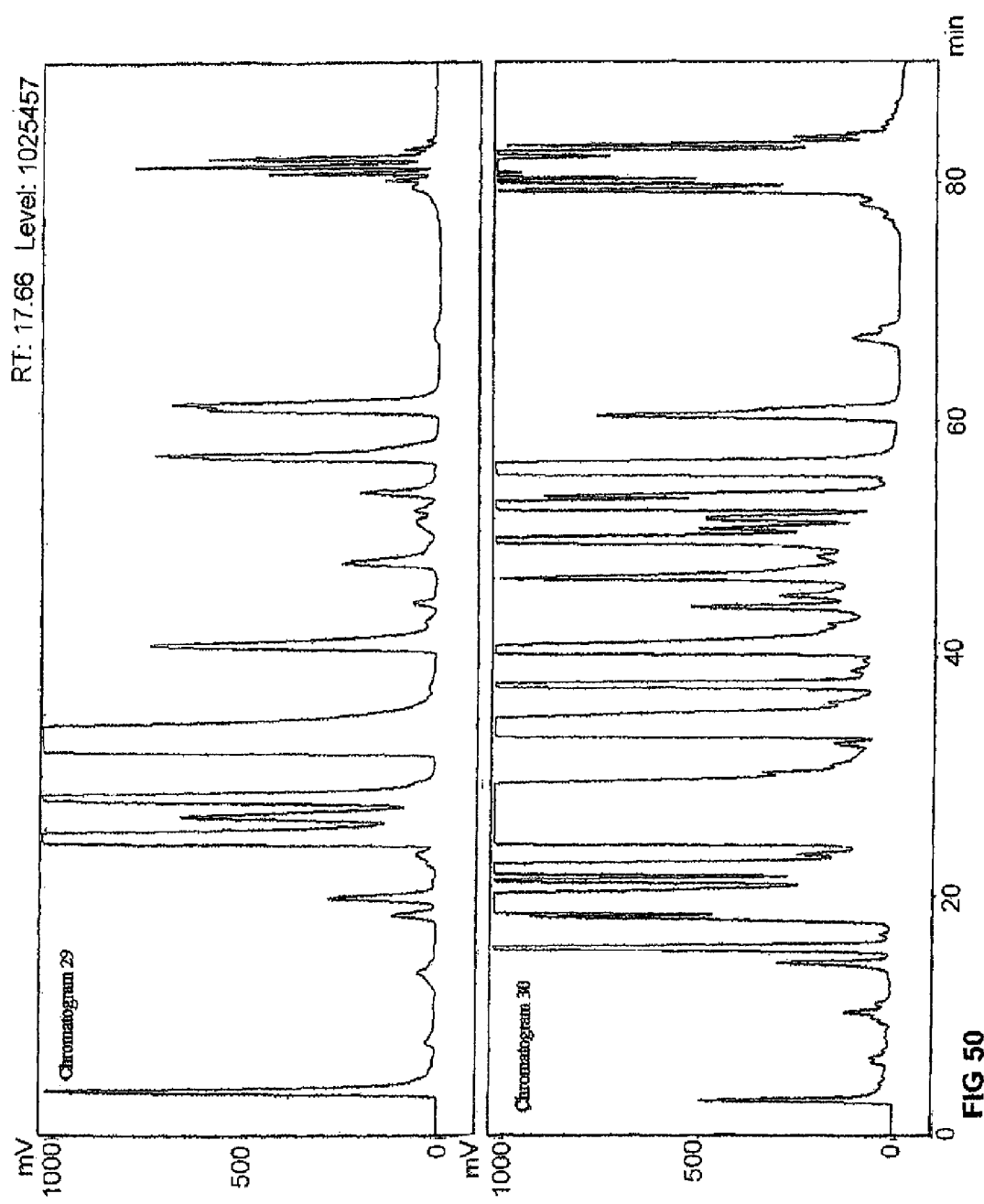
Figure 5P:
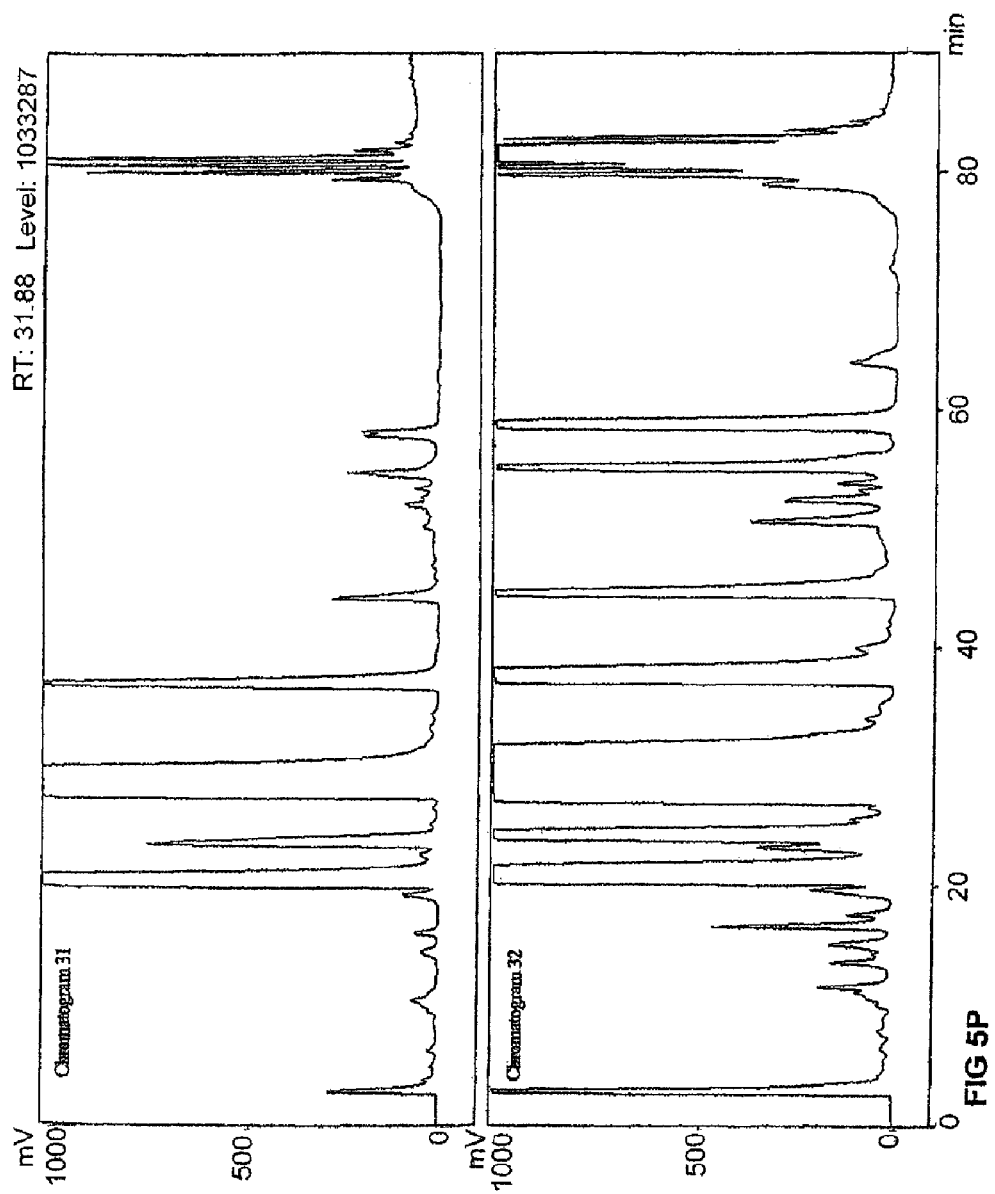

As is clear from the foregoing, this invention relates to the fungal metabolism/transformation of lipid substrates. The fungi can be endogenous or exogenous to the lipid substrate. However, only fungi with very specific capabilities will grow on lipid substrates. Not all have the potential to transform the lipid substrate from which they were isolated, or other lipid substrates. Hence the present invention can utilise all fungi which grow on and metabolise/transform lipid substrates to produce oils which contain biologically-active chemical compounds.

A) Isolation of Fungi

Fungi are isolated and cultured from lipids using standard methods (see Waller et at 2002 for some common methods). Fungi can be found growing on or near the surface of naturally colonised lipidic substrates. Typically, the fungi are isolated from lipid substrates naturally colonised by the fungi and cultured onto standard agar media using standard techniques. Typically, fungi growing on the surface of lipid substrates are is obtained by removing fragments of fungus with a sterile probe and placing the fragment on media for subsequent growth and identification. Typically endogenous fungi are isolated and cultured following surface sterilisation of the lipid substrate with alcohol or hypochlorite. Fragments of the lipid substrate are then placed on media containing antibiotics to suppress bacterial growth. Emerging fungi are sub-cultured to fresh sterile media for growth and subsequent identification. Media typically include Potato Dextrose agar, Malt Extract agar, V8 juice agar, Cornmeal agar, Oatmeal agar. Typically, the fungi can be subcultured from isolation plates on the same or other standard media.

Such fungi can undergo traditional or genetic modification to enhance formation and activity of target compounds. Fungi isolated from different lipid substrates can be tested for their ability to transform different lipid substrates. Those fungi found to transform most effectively can replace less effective isolates to increase production of biologically-active compounds. These processes are used widely to enhance production of biologically active compounds and were used, for instance, to enhance production of penicillin. Enzymes can be isolated and purified from the fungi and their activity maximised using physical or chemical treatment techniques, according to R. K. Saxena, Anita Sheoran, Bhoopander Giri, W. Sheba Davidson, (2003) Review of Purification Strategies for Microbial Lipases, 52, 1-18 which is incorporated herein by reference. Enzymes are only isolated from fungi which are known to grow on and transform/metabolise lipid substrates to produce oil containing biologically-active chemical compounds.

B) Storage of Fungi and Enzymes

Fungi are stored using standard techniques such as lyophilisation, storage at low temperatures, in sterile water, on nutrient agar under oil, or desiccated (see Waller et at 2002 for some standards techniques of storing fungi).

c) Storage of Lipid Substrates

Animal and plant lipid substrates are stored in enclosed containers. Animal lipids are stored at temperatures typically below −18° C. Animal lipid substrates may be freeze-dried and ground or minced prior to storage at low temperatures.

Plant lipid substrates are stored under standard conditions of low humidity, typically below 9%, and temperature typically below 30° C.

d) Sterilisation of Animal and Plant Lipid Substrates (of Marine and Terrestrial Origin) Prior to Inoculation Prior to transformation, either animal or plant lipid substrate is sterilised in order to remove both endogenous and exogenous microbes. Sterilisation may include washing in ethanol or hypochlorite solution, gamma irradiation or its equivalent, or heat treatment (see Waller et at 2002, Plant Pathologists Pocketbook 3$^{rd}$ Edition, CABI, New York for examples of techniques in common use). In addition, lipid substrate/s may be modified by addition of specific mineral and organic additives such as found in Czapek Dox agar (see Waller for a recipe for Czapek Dox, a commonly used mineral supplement).

e) Inoculation of Lipid Substrate

Depending on the fungi population of the lipid substrate it is frequently possible to simply metabolise/transform the lipid substrate using the conditions specified below, without further inoculation of the substrate.

The lipid substrate is inoculated with one or more fungi or their enzymes as required. The substrate may be sliced, minced, chopped or ground to enable it to be spread in a layer typically between 0.5 and 10 cm on a surface that may be a stainless steel trays, or with the base perforated to allow oxygen to the lower surface and oil to drip from the substrate and be collected in a suitable container or an equivalent system. Inoculation uses standard procedures (see Waller et at 2002) including spraying or painting the lipid surface with fungal spores suspended in sterile water. The inoculated lipid substrate is incubated at a temperature between 4-35° C. commonly around 5-20° C., and a relative humidity between 80-100%, typically 95%. The substrate is then typically incubated for a period between 7 days and about 120 days, and typically between 7, 14, 28, 35, 42, 56, 63 days.

f) Production of Oils and Extraction of Biologically Active Compounds

The lipid substrate used during fungal metabolism will determine the method used to extract the biologically active oil. The four main methods that may be used are: temperature rendering, supercritical fluid extraction, solvent extraction and cold pressing. The last method is used only in respect of the production of plant oils.

Following incubation the animal lipid substrate containing the fungi is minced or ground and transferred to a stainless vessel prior to the rendering process. This process typically involves rendering at a temperature between 40-80° C., usual temperature set around 70-75° C. with constant slow speed stirring until the lipid substrate has melted into oil; heating may be electrical, or by steam or hot water. The liquid in the vessel that contains the oil is then centrifuged, followed by filtration. The residue that remains from the centrifuging step may then be subjected to further extractions, generally using standard procedures used in the plant-seed oil and pharmaceutical industries as well as in natural product isolations used in research. The filtrate, which contains the biologically active oil, is then heated for a further period of between 15 minutes and about 8 hours at temperatures ranging from 100 to about 160° C. under inert gas atmosphere or at normal atmospheric conditions. Typical conditions that are commonly used are 135° C. for 2 hours under inert gas atmosphere such as nitrogen. This step sterilises the oil, and in addition denatures any protein/s present. After cooling to a suitable temperature using a heat exchanger the oil is then filtered again to remove any residual precipitated protein and/or fungi particulate which may be present. The oil is packaged into 20 and or 200 litre pharmaceutical grade drums for storage. For extraction of biologically active compounds from oil refer to FIG. 1.

In the case of plant seed, nut oils or other lipid sources not of animal origin the inoculated and incubated lipid substrate/s containing fungi may be minced or ground prior to cold pressing using a screw press, the oil from the screw press then being centrifuged and filtered. This oil is heated for a further period of between 15 minutes and about 8 hours at temperatures ranging from 100 to about 160° C. under inert gas atmosphere or at normal atmospheric conditions. Typical conditions commonly used are 135° C. for 2 hours under inert gas atmosphere such as nitrogen. This step sterilises the oil, and in addition denatures any protein/s that may be present. After cooling to a suitable temperature using a heat exchanger the oil is filtered again to remove any residual precipitated protein and/or fungi particulate. The oil is packaged into 20 and or 200 litre pharmaceutical grade drums for storage. The cake from the press is solvent extracted using a range of common solvents selected from such as hexane, isohexane, petroleum spirits, methanol, isopropanol, propanol, ethanol and diethyl ether. The solvent is then removed by evaporation and recovered for future use. The techniques used are standard in plant oil industry. The oil produced is then treated as described for animal substrates.

The oil obtained from the above processes may then be subjected to solvent extraction at various temperatures typically using one or more of the following solvents:

methanol, ethanol, propanol, isopropanol, diethyl ether, light petroleum spirits, butanol, acetone and acetonitrile. This procedure involve mixing the oil on a mass or volume basis in the ratio of 1/1 or 2/1 solvent to oil then cooling to a temperature of between 0° C. to −40° C. for a time period from 30 minutes up to 24 hours. The solvent containing the biologically-active molecules is decanted or poured off, centrifuged (if required) and evaporated dryness to obtain the extract. Typical conditions on a laboratory scale 100 gm of oil is thoroughly mixed with 100 gm methanol and held at 0° C. for 16 hours, then centrifuged if required and solvent evaporated using a rotary film evaporator. The resulting residue contains the biologically-active chemical compounds. Solvent should be recovered for recycling.

Forms of Administration:

It is possible in the pharmaceutical composition of the inventive subject matter for the dosage form to combine various forms of release, which include without limitation, immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is performed using well known procedures and techniques available to the ordinary artisan. Each of these specific techniques or procedures for obtaining the release characteristics is well known to those persons skilled in the art. As used herein, a "controlled release form" means any form having at least one component formulated for controlled release. As used herein, "immediate release form" means any form having at least some of its pharmaceutically active components formulated for immediate release.

A variety of administration routes are available and the route selected will depend on the particular condition being treated and the dosage required for therapeutic efficacy. In the methods and compositions of the present invention, any mode of administration is acceptable and include oral, rectal, topical, nasal, transdermal or parenteral (e.g. subcutaneous, intramuscular and intravenous) routes.

Any biologically-acceptable dosage form, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, lard gelatin capsules, caplets, lozenges, chewable lozenges, beads, powders, granules, particles, microparticles, dispersible granules, cachets, douches, suppositories, creams, lotions, topicals, inhalants, aerosol inhalants, patches, particle inhalants, implants, depot implants, ingestibles, injectables, infusions, functional foods and combinations thereof. The preparation of the above dosage is well known to those persons skilled in the art. Generally, each would contain a predetermined amount of the active component in association with a carrier which constitutes one or more appropriate ingredients.

Compositions suitable for parenteral administration conveniently comprise a sterile aqueous preparation of the active component which is formulated according to known methods using suitable dispersing and suspending agents. A sterile injectable preparation may be formulated as a solution or suspension in a non-toxic parenterally acceptable diluent or solvent (e.g. water, isotonic sodium chloride solution). Sterile fixed oils can also be employed as a solvent or suspending medium.

Typical dosages:—(a) extracts (from 0.01 mg to 1000 mg per kilogram) several doses taken orally may be necessary throughout the day, (b) oil (from 5 mL to 20 mL per day) taken orally in 5 mL doses. Initial loading doses of up to 30 or 40 ml of pure oil per day is also typical. Multiple daily doses are contemplated to achieve appropriate systemic levels of the active component. The formulation of therapeutic compositions is well known to persons skilled in this field. Suitable pharmaceutically acceptable carriers and/or diluents include any and all conventional solvents, dispersion media, fillers, solid carriers, aqueous solutions, coatings, isotonic and absorption delaying agents and the like. Such formulations and formulating is described in Remingtons's Pharmaceutical Sciences (18$^{th}$ Edn), Mack Publishing CO, Pennsylvania, USA.

EXAMPLES

A) Preparation of Topical Medicaments Using Biologically-Active Oils

Examples of creams for topical application were prepared according to the following protocols:

Formulation 1

| | DESCRIPTION | COMPOSITION (% w/w) |
|---|---|---|
| PHASE A | | |
| Water | Water | 52.475 |
| Glycerol | Glycerol | 3.000 |
| Disodium EDTA | Disodium EDTA | 0.100 |
| Stabileze QM ™ | Poly(methyl vinyl ether/maleic anhydride) decadiene crosspolymer | 0.350 |
| PHASE B | | |
| Oil | Biologically-active oil | 30.000 |

-continued

Formulation 1

| | DESCRIPTION | COMPOSITION (% w/w) |
|---|---|---|
| Prolipid 141 ™ | Emulsifier blend of stearic acid, behenyl alcohol, glycerol-monostearate, lecithin, C12-C16 alcohols and palmitic acid | 5.000 |
| Cerasynt 840 ™ | PEG-20 stearate | 1.000 |
| Ceraphyl 230 ™ | Di-isopropyl adipate | 4.000 |
| Vitamin E acetate | Vitamin E acetate | 0.200 |
| PHASE C | | |
| 10% w/v NaOH | Sodium hydroxide | 0.875 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

1. In phase A combine water, disodium EDTA, and glycerol, then mix thoroughly.
2. Sprinkle Stabileze QM™ into the pre-mixed solution with stirring at room temperature, until uniformly dispersed. Then heat to 75-80° C. while stirring, for at least 30 minutes.
3. In a separate vessel, combine ingredients of phase B; mix and heat to 75-80° C.
4. Add phase B to phase A, homogenise for 3-5 minutes, then turn off the heat source.
5. Add phase C into homogenate of phases A & B and then homogenise for 3-5 minutes with no further heating.
6. Remove homogeniser and thoroughly mix, while cooling to 38-40° C.
7. Add phase D to batch and mix until uniform.
8. Adjust for water loss and mix until uniform.

Notes (a) Adjustments to the amounts of preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Cerasynt 840, Ceraphyl 230, Prolipid 141 and Liquapar Optima are trade marks of International Specialty Products, Inc. 1361 Alps Road Wayne N.J. 07470

Formulation 2

| | DESCRIPTION | COMPOSITION (% w/w) |
|---|---|---|
| PHASE A | | |
| Water | Water | 51.950 |
| Glycerol | Glycerol | 3.000 |
| Disodium EDTA | Disodium EDTA | 0.100 |
| Stabileze QM ™ | Poly(methyl vinyl ether/maleic anhydride) decadiene crosspolymer | 0.500 |
| PHASE B | | |
| Oil | Biologically-active oil | 25.000 |
| Neem seed oil | Neem seed oil | 4.000 |
| Tea tree oil | Tea tree oil | 1.000 |

Formulation 2 (continued)

| | DESCRIPTION | COMPOSITION (% w/w) |
|---|---|---|
| Prolipid 141 ™ | Emulsifier blend of stearic acid, behenyl alcohol, glycerol-monostearate, lecithin, C12-C16 alcohols and palmitic acid | 5.000 |
| Cerasynt 840 ™ | PEG-20 stearate | 1.000 |
| Ceraphyl 230 ™ | Di-isopropyl adipate | 4.000 |
| Vitamin E acetate | Vitamin E acetate | 0.200 |
| PHASE C | | |
| 10% w/v NaOH | | 1.250 |
| Water | | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

9. In phase A combine water, disodium EDTA and glycerol, then mix thoroughly.
10. Sprinkle Stabileze QM™ into the pre-mixed solution with stirring at room temperature, until uniformly dispersed. Then heat to 75-80° C. while stirring, for at least 30 minutes.
11. In a separate vessel, combine ingredients of phase B; mix and heat to 75-80° C.
12. Add phase B to phase A, homogenise for 3-5 minutes, then turn off the heat source.
13. Add phase C into homogenate of phases A & B and then homogenise for 3-5 minutes with no further heating.
14. Remove homogeniser and thoroughly mix, while cooling to 38-40° C.
15. Add phase D to batch and mix until uniform.
16. Adjust for water loss and mix until uniform.

Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Cerasynt 840, Ceraphyl 230, Prolipid 141 and Liquapar Optima are trade marks of International Specialty Products, Inc. 1361 Alps Road Wayne N.J. 07470

Formulation 3.

| | DESCRIPTION | COMPOSITION (% w/w) |
|---|---|---|
| PHASE A | | |
| Water | Water | 46.425 |
| Glycerol | Glycerol | 3.000 |
| Disodium EDTA | Disodium EDTA | 0.100 |
| Stabileze QM ™ | Poly(methyl vinyl ether/maleic anhydride) decadiene crosspolymer | 0.650 |
| PHASE B | | |
| Oil | Biologically-active oil | 25.000 |
| Neem seed oil | Neem seed oil | 5.000 |
| Cerasynt 945 ™ | Glyceryl stearate & Laureth 23 | 6.000 |
| Cerasynt 840 ™ | PEG-20 stearate | 4.000 |
| Ceraphyl 230 ™ | Di-isopropyl adipate | 5.000 |
| Vitamin E acetate | Vitamin E acetate | 0.200 |
| PHASE C | | |
| 10% w/v NaOH | Sodium hydroxide | 1.625 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

17. In phase A combine water, disodium EDTA and glycerol, then mix thoroughly.
18. Sprinkle Stabileze QM™ into the pre-mixed solution with stirring at room temperature, until uniformly dispersed. Then heat to 75-80° C. while stirring, for at least 30 minutes.
19. In a separate vessel, combine ingredients of phase B; mix and heat to 75-80° C.
20. Add phase B to phase A, homogenise for 15 minutes, then turn off the heat source.
21. Add phase C into homogenate of phases A & B and then homogenise for 3-5 minutes without further heating.
22. Remove homogeniser and thoroughly mix, while cooling to 38-40° C.
23. Add phase D to batch and mix until uniform.
24. Adjust for water loss and mix until uniform.

Notes
(a) Adjustments to the amount of preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Cerasynt 945, Cerasynt 840, Ceraphyl 230, Prolipid 141 and Liquapar Optima are trade marks of International Specialty Products, Inc. 1361 Alps Road Wayne N.J. 07470

Formulation 4

| | DESCRIPTION | COMPOSITION (% w/w) |
|---|---|---|
| PHASE A | | |
| Water | Water | 51.475 |
| Glycerol | Glycerol | 3.000 |
| Disodium EDTA | Disodium EDTA | 0.100 |
| Stabileze QM ™ | Poly(methyl vinyl ether/maleic anhydride) decadiene crosspolymer | 0.350 |
| PHASE B | | |
| Oil | Biologically active oil | 25.000 |
| Neem seed oil | Neem seed oil | 4.000 |
| Tea tree oil | Tea tree oil | 1.000 |
| Prolipid 141 ™ | Emulsifier blend of stearic acid, behenyl alcohol, glycerol- | 5.000 |

-continued

Formulation 4

| DESCRIPTION | | COMPOSITION (% w/w) |
|---|---|---|
| | monostearate, lecithin, C12-C16 alcohols and palmitic acid | |
| Cerasynt 840 ™ | PEG-20 stearate | 1.000 |
| Ceraphyl 230 ™ | Di-isopropyl adipate | 4.000 |
| Vitamin E acetate | Vitamin E acetate | 0.200 |
| PHASE C | | |
| 10% w/v NaOH | Sodium hydroxide | 0.875 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

25. In phase A combine water, disodium EDTA and glycerol, then mix thoroughly.
26. Sprinkle Stabileze QM™ into the pre-mixed solution with stirring at room temperature, until uniformly dispersed. Then heat to 75-80° C. while stirring, for at least 30 minutes.
27. In a separate vessel, combine ingredients of phase B; mix and heat to 75-80° C.
28. Add phase B to phase A, homogenise for 3-5 minutes, then turn off the heat source.
29. Add phase C into homogenate of phases A & B and then homogenise for 3-5 minutes with no further heating.
30. Remove homogeniser and thoroughly mix, while cooling to 38-40° C.
31. Add phase D to batch and mix until uniform.
32. Adjust for water loss and mix until uniform.

Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Cerasynt 840, Ceraphyl 230, Prolipid 141 and Liquapar Optima are trade marks of International Specialty Products, Inc. 1361 Alps Road Wayne N.J. 07470

Formulation 5

| DESCRIPTION | | COMPOSITION (% w/w) |
|---|---|---|
| PHASE A | | |
| Water | Water | 51.475 |
| Glycerol | Glycerol | 3.000 |
| Disodium EDTA | Disodium EDTA | 0.100 |
| Stabileze QM ™ | Poly(methyl vinyl ether/maleic anhydride) decadiene crosspolymer | 0.350 |
| PHASE B | | |
| Oil | Biologically-active oil | 25.000 |
| Neem seed oil | Neem seed oil | 4.000 |
| Tea tree oil | Tea tree oil | 1.000 |
| Prolipid 141 ™ | Emulsifier blend of stearic acid, behenyl alcohol, glycerol- | 5.000 |

-continued

Formulation 5

| DESCRIPTION | | COMPOSITION (% w/w) |
|---|---|---|
| | monostearate, lecithin, C12-C16 alcohols and palmitic acid | |
| Cerasynt 840 ™ | PEG-20 stearate | 1.000 |
| Eucalyptus oil | Eucalyptus oil | 4.000 |
| Vitamin E acetate | Vitamin E acetate | 0.200 |
| PHASE C | | |
| 10% w/v NaOH | Sodium hydroxide | 0.875 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

33. In phase A combine water, disodium EDTA and glycerol, then mix thoroughly.
34. Sprinkle Stabileze QM™ into the pre-mixed solution with stirring at room temperature, until uniformly dispersed, then heat to 75-80° C. while stirring, for at least 30 minutes.
35. In a separate vessel, combine ingredients of phase B; mix and heat to 75-80° C.
36. Add phase B to phase A, homogenise for 3-5 minutes, then turn off the heat source.
37. Add phase C into homogenate of phases A & B and then homogenise for 3-5 minutes with no further heating.
38. Remove homogeniser and thoroughly mix, while cooling to 38-40° C.
39. Add phase D to batch and mix until uniform.
40. Adjust for water loss and mix until uniform.

Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Cerasynt 840, Ceraphyl 230, Prolipid 141 and Liquapar Optima are trade marks of International Specialty Products, Inc. 1361 Alps Road Wayne N.J. 07470

FORMULATION 6

| DESCRIPTION | | COMPOSITION (% w/w) |
|---|---|---|
| PHASE A | | |
| Water | Water | 53.525 |
| Glycerol | Glycerol | 3.000 |
| Disodium EDTA | Disodium EDTA | 0.100 |
| Stabileze QM ™ | Poly(methyl vinyl ether/ maleic anhydride) decadiene crosspolymer | 0.350 |
| PHASE B | | |
| Oil | Biologically-active oil | 20.000 |
| Neem seed oil | Neem seed oil | 4.000 |
| Tea tree oil | Tea tree oil | 1.000 |
| Prolipid 141 ™ | Emulsifier blend of stearic acid, behenyl alcohol, glycerol- | 6.250 |

-continued

FORMULATION 6

| DESCRIPTION | COMPOSITION (% w/w) |
|---|---|
| monostearate, lecithin, C12-C16 alcohols and palmitic acid | |
| Vitamin E acetate    Vitamin E acetate | 0.200 |
| Ceraphyl 230 ™    Di-isopropyl adipate | 7.500 |
| PHASE C | |
| 10% w/v NaOH    Sodium hydroxide | 0.875 |
| Water    Water | 2.000 |
| PHASE D | |
| Liquapar Optima ™    Phenoxyethanol, methylparaben, Isopropylparaben, isobutylparaben butylparaben | 1.000 |
| Total | 100.000 |

Manufacturing Procedure
41. In phase A combine water, disodium EDTA and glycerol, then mix thoroughly.
42. Sprinkle Stabileze QM™ into the pre-mixed solution with stirring at room temperature, until uniformly dispersed, then heat to 75-80° C. while stirring, for at least 30 minutes.
43. In a separate vessel, combine ingredients of phase B; mix and heat to 75-80° C.
44. Add phase B to phase A, homogenise for 3-5 minutes, then turn off the heat source.
45. Add phase C into homogenate of phases A & B and then homogenise for 3-5 minutes with no further heating.
46. Remove homogeniser and thoroughly mix while cooling to 38-40° C.
47. Add phase D to batch and mix until uniform.
48. Adjust for water loss and mix until uniform.
Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Ceraphyl 230, Prolipid 141 and Liquapar Optima are trade marks of International Specialty Products, Inc. 1361 Alps Road Wayne N.J. 07470

FORMULATION 7

| DESCRIPTION | COMPOSITION (% w/w) |
|---|---|
| PHASE A | |
| Water    Water | 53.525 |
| Glycerol    Glycerol | 3.000 |
| Disodium EDTA    Disodium EDTA | 0.100 |
| Stabileze QM ™    Poly(methyl vinyl ether/ maleic anhydride) decadiene crosspolymer | 0.350 |
| PHASE B | |
| Oil    Biologically-active oil | 20.000 |
| Neem seed oil    Neem seed oil | 4.000 |
| Tea tree oil    Tea tree oil | 1.000 |
| Prolipid 141 ™    Emulsifier blend of stearic acid, behenyl alcohol, glycerol- | 6.250 |

-continued

FORMULATION 7

| DESCRIPTION | COMPOSITION (% w/w) |
|---|---|
| monostearate, lecithin, C12-C16 alcohols and palmitic acid | |
| Ceraphyl 140A ™    Isodecyl Oleate | 7.5 |
| Vitamin E acetate    Vitamin E acetate | 0.200 |
| PHASE C | |
| 10% w/v NaOH    Sodium hydroxide | 0.875 |
| Water    Water | 2.000 |
| PHASE D | |
| Liquapar Optima ™    Phenoxyethanol, methylparaben, Isopropylparaben, isobutylparaben butylparaben | 1.000 |
| Total | 100.000 |

Manufacturing Procedure
49. In phase A combine water, disodium EDTA and glycerol, then mix thoroughly.
50. Sprinkle Stabileze QM™ into the pre-mixed solution with stirring at room temperature, until uniformly dispersed, then heat to 75-80° C. while stirring, for at least 30 minutes.
51. In a separate vessel, combine ingredients of phase B; mix and heat to 75-80° C.
52. Add phase B to phase A, homogenise for 3-5 minutes, then turn off the heat source.
53. Add phase C into homogenate of phases A & B and then homogenise for 3-5 minutes with no further heating.
54. Remove homogeniser and thoroughly mix while cooling to 38-40° C.
55. Add phase D to batch and mix until uniform.
56. Adjust for water loss and mix until uniform.
Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Ceraphyl 140A, Prolipid 141 and Liquapar Optima are trade marks of International Specialty Products, Inc. 1361 Alps Road Wayne N.J. 07470

FORMULATION 8

| DESCRIPTION | COMPOSITION (% w/w) |
|---|---|
| PHASE A | |
| Water    Water | 53.525 |
| Glycerol    Glycerol | 3.000 |
| Disodium EDTA    Disodium EDTA | 0.100 |
| Stabileze QM ™    Poly(methyl vinyl ether/ maleic anhydride) decadiene crosspolymer | 0.350 |
| PHASE B | |
| Oil    Biologically-active oil | 25.000 |
| Prolipid 141 ™    Emulsifier blend of stearic acid, behenyl alcohol, glycerol-monostearate, lecithin, C12-C16 alcohols and palmitic acid | 6.250 |
| Ceraphyl 140 ™    Isodecyl Oleate | 5.000 |

FORMULATION 8 -continued

| DESCRIPTION | | COMPOSITION (% w/w) |
|---|---|---|
| Vitamin E acetate | Vitamin E acetate | 0.200 |
| PHASE C | | |
| 10% w/v NaOH | Sodium hydroxide | 0.875 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

57. In phase A combine water, disodium EDTA and glycerol, then mix thoroughly.
58. Sprinkle Stabileze QM™ into the pre-mixed solution with stirring at room temperature, until uniformly dispersed, then heat to 75-80° C. while stirring, for at least 30 minutes.
59. In a separate vessel, combine ingredients of phase B; mix and heat to 75-80° C.
60. Add phase B to phase A, homogenise for 3-5 minutes, then turn off the heat source.
61. Add phase C into homogenate of phases A & B and then homogenise for 3-5 minutes with no further heating.
62. Remove homogeniser and thoroughly mix while cooling to 38-40° C.
63. Add phase D to batch and mix until uniform.
64. Adjust for water loss and mix until uniform.

Notes (a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(e) Stabileze QM, Ceraphyl 140A, Prolipid 141 and Liquapar Optima are trade marks of International Specialty Products, Inc. 1361 Alps Road Wayne N.J. 07470

FORMULATION 9

| DESCRIPTION | | COMPOSITION (% w/w) |
|---|---|---|
| PHASE A | | |
| Water | Water | 51.475 |
| Glycerol | Glycerol | 3.000 |
| Disodium EDTA | Disodium EDTA | 0.100 |
| Stabileze QM ™ | Poly(methyl vinyl ether/ maleic anhydride) decadiene crosspolymer | 0.400 |
| PHASE B | | |
| Oil | Biologically-active oil | 20.000 |
| Prolipid 141 ™ | Emulsifier blend of stearic acid, behenyl alcohol, glycerol-monostearate, lecithin, C12-C16 alcohols and palmitic acid | 5.000 |
| Ceraphyl 140A ™ | Isodecyl Oleate | 5.000 |
| Vitamin E acetate | Vitamin E acetate | 0.200 |

FORMULATION 9 -continued

| DESCRIPTION | | COMPOSITION (% w/w) |
|---|---|---|
| PHASE C | | |
| 10% w/v NaOH | Sodium hydroxide | 1.000 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure

65. In phase A combine water, disodium EDTA and glycerol, then mix thoroughly.
66. Sprinkle Stabileze QM™ into the pre-mixed solution with stirring at room temperature, until uniformly dispersed, then heat to 75-80° C. while stirring, for at least 30 minutes.
67. In a separate vessel, combine ingredients of phase B; mix and heat to 75-80° C.
68. Add phase B to phase A, homogenise for 3-5 minutes, then turn off the heat source.
69. Add phase C into homogenate of phases A & B and then homogenise for 3-5 minutes with no further heating.
70. Remove homogeniser and thoroughly mix while cooling to 38-40° C.
71. Add phase D to batch and mix until uniform.
72. Adjust for water loss and mix until uniform.

Notes (a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Ceraphyl 140A, Prolipid 141 and Liquapar Optima are trade marks of International Specialty Products, Inc. 1361 Alps Road Wayne N.J. 07470

FORMULATION 10

| DESCRIPTION | | COMPOSITION (% w/w) |
|---|---|---|
| PHASE A | | |
| Water | Water | 67.950 |
| Glycerol | Glycerol | 3.000 |
| Disodium EDTA | Disodium EDTA | 0.100 |
| Stabileze QM ™ | Poly(methyl vinyl ether/ maleic anhydride) decadiene crosspolymer | 0.500 |
| PHASE B | | |
| Oil | Biologically-active oil | 10.000 |
| Vitamin E | Vitamin E | 2.000 |
| Vitamin C Palmitate | Vitamin C Palmitate | 3.000 |
| Prolipid 141 ™ | Emulsifier blend of stearic acid, behenyl alcohol, glycerol-monostearate, lecithin, C12-C16 alcohols and palmitic acid | 4.000 |
| Ceraphyl 140A ™ | Isodecyl Oleate | 5.000 |
| Vitamin E acetate | Vitamin E acetate | 0.200 |

-continued

FORMULATION 10

| | DESCRIPTION | COMPOSITION (% w/w) |
|---|---|---|
| PHASE C | | |
| 10% w/v NaOH | Sodium hydroxide | 1.250 |
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure
73. In phase A combine water, disodium EDTA and glycerol, then mix thoroughly.
74. Sprinkle Stabileze QM™ into the pre-mixed solution with stirring at room temperature, until uniformly dispersed, then heat to 75-80° C. while stirring, for at least 30 minutes.
75. In a separate vessel, combine ingredients of phase B; mix and heat to 75-80° C.
76. Add phase B to phase A, homogenise for 3-5 minutes, then turn off the heat source.
77. Add phase C into homogenate of phases A & B and then homogenise for 3-5 minutes with no further heating.
78. Remove homogeniser and thoroughly mix while cooling to 38-40° C.
79. Add phase D to batch and mix until uniform.
80. Adjust for water loss and mix until uniform.
Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Ceraphyl 140A, Prolipid 141 and Liquapar Optima are trade marks of International Specialty Products, Inc. 1361 Alps Road Wayne N.J. 07470

FORMULATION 11

| | DESCRIPTION | COMPOSITION (% w/w) |
|---|---|---|
| PHASE A | | |
| Water | Water | 57.300 |
| Glycerol | Glycerol | 3.000 |
| Disodium EDTA | Disodium EDTA | 0.100 |
| Stabileze QM ™ | Poly(methyl vinyl ether/ maleic anhydride) decadiene crosspolymer | 0.400 |
| PHASE B | | |
| Oil | Biologically-active oil | 20.000 |
| Prolipid 141 ™ | Emulsifier blend of stearic acid, behenyl alcohol, glycerol-monostearate, lecithin, C12-C16 alcohols and palmitic acid | 5.000 |
| Methyl Salicylate | Methyl Salicylate | 10.000 |
| Vitamin E acetate | Vitamin E acetate | 0.200 |
| PHASE C | | |
| 10% w/v NaOH | Sodium hydroxide | 1.000 |

FORMULATION 11

| | DESCRIPTION | COMPOSITION (% w/w) |
|---|---|---|
| Water | Water | 2.000 |
| PHASE D | | |
| Liquapar Optima ™ | Phenoxyethanol, methylparaben, Isopropylparaben, isobutylparaben butylparaben | 1.000 |
| | Total | 100.000 |

Manufacturing Procedure
81. In phase A combine water, disodium EDTA and glycerol, then mix thoroughly
82. Sprinkle Stabileze QM™ into the pre-mixed solution with stirring at room temperature, until uniformly dispersed, then heat to 75-80° C. while stirring, for at least 30 minutes.
83. In a separate vessel, combine ingredients of phase B; mix and heat to 75-80° C.
84. Add phase B to phase A, homogenise for 3-5 minutes, then turn off the heat source.
85. Add phase C into homogenate of phases A & B and then homogenise for 3-5 minutes with no further heating.
86. Remove homogeniser and thoroughly mix while cooling to 38-40° C.
87. Add phase D to batch and mix until uniform.
88. Adjust for water loss and mix until uniform.
Notes
(a) Adjustments to preservative may have to be made after challenge testing.
(b) Small adjustments may have to be made to the Stabileze QM™ concentration to give correct viscosity depending on the application.
(c) Small adjustments in composition will have to be made, to allow for fragrance if required.
(d) Stabileze QM, Prolipid 141 and Liquapar Optima are trade marks of International Specialty Products, Inc. 1361 Alps Road Wayne N.J. 07470
B) Oral Formulations Containing Biologically Active Oils:
1. Hard gel capsules (0.95 mL) made of gelatine or equivalent polymer containing approximately 0.9 gm of oil containing 0.1% Tocopheryl acetate.
2. Hard gel capsules (0.95 mL) made of gelatine or equivalent polymer containing 0.50 gm of oil dispersed in macadamia oil or equivalent.
3. Soft gel capsules (1004 up to 1.0 mL capacity) made from gelatine or equivalent polymer containing from 1004, up to 1.0 mL of oil with 0.1% anti-oxidant added if required.
4. Soft gel capsules (1004 up to 1.0 mL capacity) made of gelatine or equivalent polymer containing from 10 mg up to 1000 mg of extract from the oil containing if required an anti-oxidant and another oil for example macadamia oil, soy-bean oil or equivalent.
5. Soft gel suppositories as for 3 & 4 above.
6. Syrups and lotions made from oil and extracts with the addition of other oils such is as olive, macadamia and flavours such as raspberry, strawberry, banana and with the addition of anti-oxidants if required. Dose by spoon or syringe.
7. Oral dose 5.0 mL oil by spoon or syringe.
C) In Vivo Rat Model Test Procedures Used to Analyse the Biological Activity of Various Animal and Plant Oils and their Extracts
1. Anti-inflammatory efficacy was measured in rats developing the adjuvant-induced polyarthritis, the test agents being given either transdermally or orally from the time the arthritis was first expressed. Synergistic activity with low-dosed steroid was measured either in i) rats with fully established adjuvant arthritis or ii) rats with chronic paw oedema induced by injecting 0.5 mg zymosan (in 0.2 mL saline) then waiting 3 hours for the acute oedema to peak (associated with histamine/serotonin release) and measuring residual paw swelling 21-45 hours later. For transdermal administration, oils were diluted with 0.15 vol of cineole to facilitate skin penetration and applied once daily to the shaved dorsal skin (6 cm$^2$) with brief rubbing. (See Tables 1 and 2 below).

2. Co-arthritigenic activity was measured in Dark Agouti rats by first dispersing finely-ground heat-killed *Mycobacterium. tuberculosis* in test oils (10 mg/kg) and then injecting 0.1 mL into the tailbase of female Dark Agouti rats. Signs of arthritis were recorded on day 15. Extracts from emu oils were obtained by mixing equal masses of oil and methanol then storing in a cold room or freezer at 0° C. for at least 12 hours, decanting the liquid layer, evaporating the solvent using a rotary film evaporator. Residue remaining in the flask contains the extract. These extracts were first dissolved in jojoba bean oil and diluted with an equal volume of a dispersion of *Mycobacterium. tuberculosis* (10 mg/ml) freshly prepared in jojoba bean oil. (See Table 3 below).

3. Gastroprotectant activity was ascertained in a) disease stressed (untreated) polyarthritic female Dark Agouti or Wistar rats and b) normal Dark Agouti or Wistar rats which had been fasted overnight and injected with the cholinergic drug, methacholinehydrochloride (5 mg/kg i.p.). Test materials were emulsified with 0.04% v/v Tween-20 using a Vortex homogeniser, then co-dosed with a dispersion of OTC ibuprofen (NUROFEN) 55 mg/kg used as the gastrotoxin. The stomachs were removed 2.5 hours later, briefly rinsed in saline and scored for number and severity of macroscopic haemorrhagic lesions in the gastric mucosa. (See Tables 4 and 5 below).

4. Synergistic activities of emu and macadamia oils with corticosteroids for suppressing Zymosan-induced paw oedema in rats. A single treatment of whole oil, or extract, plus either P=prednisone 2.5 mg/kg or D=dexamethasone 0.1 mg/kg in Tween-20 was administered orally 3 hours after injecting 0.5 mg zymosan into each rear paw. Data are the relative reduction in paw swelling compared with controls treated with olive oil only, expressed as percentage inhibition. (see Table 6 below).

5. For in vitro tests, oils were processed to remove the bulk of the triglycerides using solvent extraction at low temperature or solid-phase extraction in accordance with normal laboratory procedures. For in vivo tests, the oils were filtered at 22° C. to remove solids, varying from 5-45% by weight. Exceptionally stiff samples were diluted either with 0.1 volume n-octanol or up to 0.5 volumes isopropyl myristate to help 'liquefy' them, these solvents being inert vehicles for the assays described.

Note: All *Mycobacterium. tuberculosis* used is finely ground and heat killed prior to use.

Results

1. Wistar rats were injected with 0.8 mg *Mycobacterium. tuberculosis* in 00.1 mL squalene in tailbase (day 0). Treatments with biologically active oils were given either A) transdermally on days 10-13 only (4 rats/gp) or B) orally on days 15-17 together with prednisone (2.5 mg/kg, 3 rats/gp)

The changes in arthritic signs are shown below. An increase in weight is good, a decrease indicates possible toxicity. The lower the arthritic score, the better:

Note: For information on oils refer to chromatogram number and table 6 which contains process conditions.

Process conditions and chromatograph for each sample in Tables 1 to 8 are summarised in Table 11. The corresponding chromatograms are numbered 1 to 32. As an example, emu-type 2 oil in Table 3 was obtained according to the process conditions set out in line 4 of Table 11 (sample code Type 2) and the biological activity of the sample is shown in chromatogram 4.

TABLE 1

| A. Treatment (transdermal) | | Mean Changes in Arthritic Signs (Days 10→14) | | | |
|---|---|---|---|---|---|
| Sample | Dose/kg/day | Rear paw thickness | Forepaw inflammation | ΔWeight gm | Arthritis Score |
| Olive Oil - Control | 2.0 mL | 0.89 mm | 2+ | +05 | 2+ |
| Emu-A Chrom. 1. | 0.5 mL | 0.15 mm | 0.5+ | +14 | 0.5+ |
| Emu-C Chrom. 2. | 1.0 mL | 0.37 mm | 1.4+ | +18 | 1+ |
| Emu-Kalaya Chrom. 3. | 0.5 mL | 0.08 mm | −0.2+ | +05 | 0.2+ |

TABLE 2

| | | Mean Changes in Arthritic Signs (Days 15→18) | | | | |
|---|---|---|---|---|---|---|
| B. Treatment (Oral) | | Rear paw | Tail | Forepaw | ΔWeight | Arthritis |
| Sample | Dose/kg/day | thickness | thickness | inflammation | gm | Score |
| Olive Oil (OO) only - control | 2.0 mL | 0.0 mm | +0.42 mm | 0.6+ | +02 | 0.5+ |
| Prednisone with: | | | | | | |
| Olive Oil | 2.0 mL | −0.05 mm | 0.15 mm | 0.3+ | +03 | 0 |
| Emu-A Chrom. 1 | 2.0 mL | −0.59 mm | −0.82 mm | −0.8+ | 0 | −0.9+ |
| Emu-C Chrom. 2 | 2.0 mL | +0.13 mm | −0.14 mm | 0.8+ | −01 | 0.3+ |

Table 3: Arthritigenic Activity of Some Emu/Other Oils

Oils were admixed with finely ground heat-killed *M. tuberculosis* (10 mg/mL) and 0.1 mL injected into the tail base of female Dark Agouti rats.

Dispersions with jojoba bean oil contained a final concentration of only 5 mg/mL *M. tuberculosis*

Signs of arthritis were scored on day 15 for groups of 3 rats.

.

| Test Oil | Mean values for | | |
|---|---|---|---|
| | Rear paw swelling | ΔWeight | Arthritis Score |
| Olive Oil | 1.22 mm | +01 | 2.3+ |
| Lard Oil (pig) | 1.03 | +14 | 2.3+ |
| Emu-A Chrom. 1 | 0.23 | +08 | 0.5+ |
| Emu-C Chrom. 2 | 0.73 | −10 | 2+ |
| Emu-Kalaya Chrom. 3 | 0.08 | +21 | 0.7+ |
| Emu-Type 2 Chrom. 4 | 0.20 | +12 | 0.5+ |
| Jojoba Bean | 1.24 | +02 | 2.8+ |
| with extr. Emu-A (5 mg/rat) | 0.23 | +11 | 0.7+ |
| with extr. Emu-C (5 mg/rat) | 0.92 | +07 | 1.5+ |
| with extr. Emu-Ka (5 mg/rat) | 0.08 | +11 | 0.3+ |
| with extr. Emu-Ka (10 mg/rat) | 0.09 | +20 | 0.5+ |

Tables 4/5: Gastroprotective Activity of Some Emu Oils in Rats

Gastro-irritant=55 mg/kg ibuprofen given orally to animals fasted overnight, together with test emulsions=0.4 mL oil/kg prepared with 0.04% v/v Tween-20 along with or without methacholine given i.p.

A. In disease-stressed female Wistar or Dark Agouti rats with fully developed polyarthritis (on or after day 15), without methacholine.

TABLE 4

| Treatment | Gastric lesion indices in | |
|---|---|---|
| | Wistar rats n = 3/gp | Dark Agouti rats n = 4/gp |
| Tween-20 only | 32 | 44 |
| Emu-A Chrom. 1 | 07 | 22 |
| Emu-C Chrom. 2 | 21 | 51 |
| Emu-Kalaya Chrom. 3 | not tested | 27 |

B. In normal rats stimulated with Beta-methacholine (5 mg/kg in Wistar rats or 8 mg/kg in Dark Agouti rats).

TABLE 5

| Treatment | Gastric lesion indices in | |
|---|---|---|
| | Wistar rats n = 3/gp | Dark Agouti rats n = 3/gp |
| Tween-20 only | 17 | 52 |
| Emu-A Chrom. 1 | 05 | 17 |
| Emu-C Chrom. 2 | 19 | 39 |
| Emu-Kalaya Chrom. 3 | 05 | 23 |
| Olive oil (OO) | 19 | 31 |
| Extr. A = 50 mg/kg in OO | 06 | 10 |

Table 6: Synergistic Activities of Emu and Macadamia Oils with Corticosteroids for Suppressing Zymosan-Induced Paw Oedema in Rats.

A single treatment of whole oil, or extract, plus either P=prednisone 2.5 mg/kg or D=dexamethasone 0.1 mg/kg in Tween-20 was administered orally 3 hours after injecting 0.5 mg zymosan into each rear paw. Data are the relative reduction in paw swelling compared with controls treated with olive oil only, expressed as percentage inhibition.

| Treatment | Dose/ kg | Wistar rats | | Dark Agouti rats | |
|---|---|---|---|---|---|
| | | Day 1 | Day 2 | Day 1 | Day 2 |
| P + olive oil (OO) | 2 mL | 4% | 1% | 15% | 2% |
| P + Emu - A Chrom. 1 | 2 mL | 52 | 81 | 56 | 63 |
| | 0.5 | 43 | 52 | | |
| P + Emu - C Chrom. 2 | 2 mL | −05 | −16 | −14 | −12 |
| P + Lyprinol in OO | 20 mg | 57 | 31 | 65 | 66 |
| D + olive oil (OO) | 2 mL | 05 | 0 | | |
| D + Emu - A Chrom. 1 | 2 mL | 77 | 40 | | |
| D + Emu - C Chrom. 2 | 2 mL | 22 | −15 | | |
| D + Lyprinol in OO | 20 mg | 56 | 50 | | |
| P + Olive oil (OO) | 2.0 mL | 0 | | | |
| P + Macadamia - 19 Chrom. 30 | 1.6 mL | 1 | | | |
| P + Macadamia - 20 Chrom. 31 | 1.6 mL | 41 | | | |
| P + Oleic acid (90%) | 2.0 mL | −11 | | | |
| P + Isostearic acid (comm.) | 2.0 mL | 39 | | | |
| P + Lyprinol in OO | 20 mg | 46 | | | |

D) In-vitro Lipoxygenase Assays of Several Different Oil Samples

Neutrophil 5-Lipoxygenase Pathway

Overview

Arachidonic acid is converted into eicosanoids (or prostanoids) by two major pathways, the 5-lipoxygenase pathway, which leads to the formation of leukotrienes, and the cyclo-oxygenase pathway which leads to the formation of prostaglandins and thromboxanes. Some, but not all, of the products of both of these pathways have potent pro-inflammatory properties. For example, $LTB_4$ is a very potent chemotactic agent, and its peptido-metabolites, $LTC_4$, $LTD_4$ and $LTE_4$, which were originally known as "slow reacting substance of anaphylaxis" or SRS-A, are potent bronchoconstrictor agents.

Many of the currently used anti-inflammatory drugs, in particular the non-steroidal anti-inflammatory drugs (NSAIDS), function via the inhibition of the cyclo-oxygenase pathway. More recently, considerable effort around the world has focused on the development of inhibitors of the lipoxygenase pathway, or of dual inhibitors that block both pathways.

The principal steps of the 5-lipoxygenase pathway of these cells is shown in FIG. 3. In this pathway, arachidonic acid (AA), from membrane phospholipids, is released via the action of phospholipase $A_2$ ($PLA_2$). This AA is then substrate for the first enzyme in the pathway—5 lipoxygenase, which converts it to 5-hydroperoxyeicosatetraenoic acid (5-HPETE). 5-HPETE is then converted enzymatically to either 5-hydroxyeicosa-tetraenoic acid (5-HETE) by glutathione peroxidase, or to leukotriene $A_4$ ($LTA_4$) by $LTA_4$ synthase. $LTA_4$ is then converted either non-enzymatically to the all trans isomers of $LTB_4$, or hydrolysed by $LTA_4$ hydrolase to leukotriene $B_4$ ($LTB_4$). Human PMN do not significantly metabolise $LTB_4$ any further, although other cells, such as eosinophils convert it to the potent vasoconstrictor peptido-leukotrienes, SRS-A.

The Lipoxygenase Pathways (Leukotrienes and HETE) Assay

The HPLC assay readily quantifies 5-HETE, 12-HETE, $LTB_4$, and the two all trans-isomers of $LTB_{-4}$, and thus gives quantitative data on the relative activities of the enzymes in the 5-lipoxygenase of neutrophils, as well as data on the 12-lipoxygenase pathway of platelets. Thus it is an ideal system to test potential inhibitors of these pathways.

The effects of inhibitory compounds may be tested on isolated human PMN and platelets, in which the pathways are activated by treating the PMN or platelets with arachidonic acid and the calcium ionophore $A_{23187}$. The addition of arachidonic acid eliminates the $PLA_2$ step, and provides high levels of substrate for the pathway. Furthermore, such activation is known to maximally drive the pathway to produce the greatest synthesis of all the metabolites, and thus is also the least sensitive to inhibition. Hence, compounds that do inhibit the pathway activated in this fashion are potentially potent inhibitors.

Preparation of Test Samples

All samples were dissolved in ethanol to give stock solutions of 10 mg/mL. Two further dilutions of each stock solution were made in ethanol at 5 and 1 mg/mL, making 10 test samples in all.

10 µL of each of the diluted stocks was added to 1000 µL of PMN suspension in Hank's Buffer, to give final test concentrations of 5, 10 and 50 ug/mL as required for the analysis.

Preparation of Human Neutrophils (PMN)

1. Up to 100 mL of blood was taken from a normal volunteer and anticoagulated with EDTA. Two mL of 4.5% EDTA in water was mixed with each 10 mL of blood.
2. A further 2 mL of 6.0% Dextran T500 was added to each of the 12 mL mixtures in 1, and placed in a water bath at 37° C., to sediment the red blood cells.
3. Following sedimentation in 2, the supernatant was carefully laid over 5 mL of Percoll, density 1.070. This was then spun at 500 g for 35 mins.
4. All the cells (PMN and remaining RBC) below the Percoll interface were removed with a plastic pipette and diluted at least 3-fold with $Ca^{2+}/Mg^{2+}$-free Dulbecco's phosphate buffer, and centrifuged at 600 g for 10 mins.
5. Following 4, the supernatant was carefully aspirated, and the pellet gently mixed with 1 mL of $Ca^{2+}/Mg^{2+}$-free Dulbecco's phosphate buffer by aspiration/deaspiration into a 1 ml plastic disposable pipette. A further 40 mL of $Ca^{2+}/Mg^{2+}$-free Dulbecco's phosphate buffer was then added and mixed by inversion. The cell suspension was then centrifuged at 600 g for 10 mins.
6. Following centrifugation, the supernatant was removed and the PMN pellet lysed with 10 mL of a 0.2% cold sodium chloride solution for 20 secs, followed by the addition of 10 mL of a 1.6% cold sodium chloride solution, and centrifuged at 600 g for 10 mins.
7. Following 6, the PMN pellet was vigorously mixed with 1 mL of Hank's buffer by rapid aspiration/deaspiration into a 1 mL plastic disposable pipette, and then finally suspended in Hank's buffer at $2.4 \times 10^6$ PMN/ml (as measured using a Coulter counter), in preparation for the leukotriene assay.

Activation of Leukotriene Pathway 1. 1 mL of PMN suspension ($2.4 \times 10^6$ PMN/ml) was transferred to a 13 mL glass tube (chromic acid washed) and placed in a water bath at 37° C. for 5 min prewarming.
2. Following prewarming, at time zero, 10 µL of each test compound in methanol (or equivalent volumes of methanol as control) was added to quadruplicate tubes over a 20 sec period.
3. At 5 min, 5 µL of 2 mM arachidonic acid (10 µM final) was added (4 tubes/20 secs).
4. At 10 min, 5 µL of 1 mM calcium ionophore ($A_{23187}$) (5 µM final) was added (4 tubes/20 secs).
5. At 15 min the reaction was terminated by the addition of 100 µL 100 mM citric acid. This lowers the pH of the aqueous phase to less than 3, which is necessary for the extraction of the leukotrienes into the organic phase.
6. The pH of several samples was checked to ensure pH<3.0. (This is important).
7. 40 ng Prostaglandin B2 and 166 ng 15-HETE were added to each tube as the internal standard for LTB4 and 5-HETE respectively, and samples were mixed.
8. For Standard Curves LTB4 [1 ng/µl] (for a standard curve in the range 0-50 ng) and 5-HETE [5 ng/µL] (standard curve range 0-250 ng) were added to tubes containing 1 mL PMN, 100 µA of 100 mM citric acid and 40 ng $PGB_2$ and 166 ng 15-HETE.
9. All tubes were vortexed.
10. 5 mL chloroform/methanol (7:3) was added and the tubes vortexed vigorously for 30 secs, then centrifuged for 10 min at 2000 rpm.
11. Approx. 3.5 mL of the lower chloroform layer (containing the extracted leukotrienes and hydroxy acids (HETES), as well as the internal standards) was transferred to a 3 mL borosilicate glass tube and the chloroform evaporated in a Savant centrifugal evaporator, under vacuum, at room temperature.
12. The samples were reconstituted in 100 µL of the $LTB_4$ mobile phase, vortexed and transferred to Waters low volume inserts for injection (usually <25 µl).
13. The HPLC was setup for the $LTB_4$ conditions, and all the samples assayed for $LTB_4$ and the all trans isomers of $LTB_4$.

HPLC Assay for Leukotrienes and Hydroxy Acids

Mobile Phases

LTB4 Assay: 70% Methanol/30% $H_2O$/0.08% Acetic Acid (pH adjusted to 6.2 with ammonium hydroxide).

5-HETE Assay: 80% Methanol/20% $H_2O$/0.08% Acetic Acid (pH adjusted to 6.2 with ammonium hydroxide).

HPLC Conditions

Wavelength: 270 nm ($LTB_4$), 234 nm (5-HETE)

Analysis: Water's Millennium

Flow Rate: 1 mL/min

Column and Guard Pak: $C_{18}$ Nova Pak

LTB4 Assay

Retention Times

Prostaglandin B2-4.6 min 6-trans-leukotriene $B_4$-6.6 min 6-trans-epi-leukotriene B4-7.4 min Leukotriene $B_4$-8.7 min Full Chemical Names of $LTB_4$ and its 6-Trans Isomers Leukotriene B4: (5S,12R)-Dihydroxy-(Z,E,E,Z)-6,8,10,14-eicosatetraenoic acid.

6-trans-Leukotriene B4: (5S,12R)-Dihydroxy-(E,E,E,Z)-6,8,10,14-eicosatetraenoic acid.

6-trans-12-epi-LeukotrieneB4:(5S,12S)-Dihydroxy-(E,E,E,Z)-6,8,10,14-eicosatetraenoic acid 5-HETE Assay Retention Times 15-HETE-6.3 min 5-HETE-8.5 min Full Chemical Names 15-HETE: 15(S)-Hydroxy-(Z,Z,Z,E)-5,8,11,13-eicosatetraenoic acid 5-HETE: 5(S)-Hydroxy-(E,Z,Z,Z)-6,8,11,14-eicosatetraenoic acid

TABLE 7

Effects of Emu Oil Methanol Extracts and pure 12-methyl tetradecanoic acid (12-MTA) on Leukotriene Synthesis (Expressed as a percentage of the methanol control)

| Test Material | Dilution | Isomer 1 | Isomer 2 | $LTB_4$ | 5-HETE |
|---|---|---|---|---|---|
| Control | | 100 ± 22 | 100 ± 22 | 100 ± 4 | 100 ± 4 |
| Emu-Type 2 Chrom. 4 | 50 µg/mL | 0 | 0 | 11 ± 8 | 10 ± 5 |
| Emu-Type 2 Chrom. 4 | 10 µg/mL | 88 ± 12 | 71 ± 11 | 74 ± 6 | 76 ± 16 |
| Emu-Type 2 Chrom. 4 | 5 µg/ml | 94 ± 12 | 99 ± 13 | 84 ± 10 | 102 ± 2 |
| Emu-Type 2* Chrom. 4 | 50 µg/mL | 23 ± 3 | 20 ± 4 | 17 ± 11 | 16 ± 11 |
| Emu-Type 2* Chrom. 4 | 10 µg/mL | 78 ± 6 | 76 ± 7 | 80 ± 4 | 78 ± 7 |
| Emu-Type 2* Chrom. 4 | 5 µg/mL | 95 ± 9 | 96 ± 8 | 88 ± 2 | 90 ± 7 |
| Emu-Type-B Chrom. 24 | 50 µg/mL | 0 | 0 | 0 | 4 ± 2 |
| Emu-Type-B Chrom. 24 | 10 µg/mL | 82 ± 14 | 86 ± 14 | 88 ± 9 | 66 ± 9 |
| Emu-Type-B Chrom. 24 | 5 µg/mL | 110 ± 11 | 137 ± 9 | 95 ± 8 | 92 ± 1 |
| 12-MTA | 50 µg/mL | 0 | 0 | 0 | 0 |
| 12-MTA | 20 µg/mL | 0 | 0 | 0 | 2 ± 4 |
| 12-MTA | 10 µg/mL | 59 ± 14 | 68 ± 14 | 70 ± 17 | 46 ± 11 |
| 12-MTA | 5 µg/mL | 101 ± 12 | 97 ± 9 | 101 ± 12 | 65 ± 3 |
| 12-MTA | 2 µg/mL | 73 ± 13 | 60 ± 17 | 84 ± 5 | 55 ± 9 |

*Prior to extraction the original oil sample was treated by passing nitrogen gas at high flow rate through oil heated at 135° C. for two hours with rapid stirring, to remove volatile compounds.

TABLE 8

Effects of Fatty acid methyl ester of emu oil, methanol extracts of emu and ostrich oil produced by fungal inoculation and incubation on Leukotriene Synthesis (Expressed as a percentage of the methanol control)

| Test Material | Dilution | Isomer 1 | Isomer 2 | $LTB_4$ | 5-HETE |
|---|---|---|---|---|---|
| Control | | 100 ± 9 | 100 ± 10 | 100 ± 6 | 100 ± 5 |
| Fatty acid methyl ester of emu oil* | 50 µg/mL | 7 ± 0.5 | 0 | 8 ± 1 | 6 ± 2 |
| Fatty acid methyl ester of emu oil* | 10 µg/mL | 103 ± 9 | 103 ± 8 | 95 ± 6 | 105 ± 4 |
| Emu oil-WB methanol extract Chrom. 21 | 50 µg/mL | 4 ± 0.5 | 0 | 0 | 23 ± 4 |
| Emu oil-WB methanol extract Chrom. 21 | 10 µg/mL | 61 ± 2 | 65 ± 2 | 80 ± 3 | 85 ± 3 |
| Ostrich oil methanol extract Chrom. 22 | 50 µg/mL | 9 ± 2 | 14 ± 3 | 22 ± 6 | 21 ± 8 |
| Ostrich oil methanol extract Chrom. 22 | 10 µg/mL | 56 ± 12 | 74 ± 17 | 65 ± 11 | 83 ± 13 |

*Fatty acid methyl ester (FAME) of emu oil sample A, Chromatogram 1.

Results and Discussion

The data shows that all three samples in table were potent inhibitors of the 5-LOX pathway. The data are compared to 12-methyl tetradecanoic acid which showed 100% inhibition as low as 20 µg/mL.

With respect to samples in Table 8, FAME sample was the least effective, where as Emu oil-WB and Ostrich oil samples are approximately the same as the three samples in Table 7. This confirms that the process for the production of biologically-active oils may be reproduced using different lipid substrates etc.

E) In-vitro Prostaglandin $PGE_2$ (COX Pathways) Assay Oil Samples

This assay was performed using Cayman chemicals Prostaglandin $E_2$ EIA Kit-Monoclonal, according to kit protocol. Each sample was assayed at three dilutions in duplicate. As can be seen from Table 9 the inhibition of the $PGE_2$ response to aspirin (50 µM) was around 72.6% of the control value. In particular the two samples produced dose dependent inhibition of secreted $PGE_2$ from the mouse fibroblast cell line equivalent to or better than aspirin under the test conditions.

TABLE 9

Percent Inhibition of Secreted $PGE_2$ from 3T3 cells exposed to Oil Extracts

| Sample | Concentration µg/mL | % Control |
|---|---|---|
| DMSO + A23187 | | 100 |
| Aspirin | 50 µM | 72.6 |
| Emu Oil Extract - P3 Chrom. 3 | 100 | 52 |
| Emu Oil Extract - P3 Chrom. 3 | 20 | 59 |
| Emu Oil Extract - P3 Chrom. 3 | 4 | 84.8 |
| Lyprinol - P10 | 100 | 60.9 |
| Lyprinol - P10 | 20 | 83.6 |
| Lyprinol - P10 | 4 | 84.6 |

F) Examples of Therapeutic Activity

1) Patient suffering from ulcerative colitis for seven years had experienced chronic diarrhea and daily rectal bleeding. Patient ingested 5 mL of fungi-derived biologically-active emu oil twice daily. All anal bleeding associated with the ulcerative colitis disappeared after 2 months. This patient has also responded to fungi-derived biologically-active ostrich oil.

2) Patient suffering chronic pain from intestinal and duodenal ulcers ingested 5 mL of fungi-derived biologically-active emu oil twice daily and pain has ceased. Patient also observed that his unstable diabetes became more responsive to the insulin resulting in a reduction of dosage required.

3) Patient diagnosed with Crohn's disease 5 years ago and was suffering ongoing abdominal pain, diarrhoea or constipation, rectal bleeding, cold sweats and lethargy. After weeks ingesting 5 mL of fungi derived biologically-active emu oil twice daily. The patient's Crohn's disease is in remission (this has been confirmed by medical tests) with no further abdominal pains, diarrhoea or constipation.

4) Patient diagnosed with breast cancer, had lumpectomy, radiation and chemotherapy. Topical application of cream produced from fungi-derived biologically-active oil applied three times daily which reduced pain and inflammation in the breast.

5) Patient is a 54 year old Caucasian male with a 10 year history of mild to moderate asthma, which was controlled with 400 ug twice daily of beclomethasone and either salbutamol or turbutamine bronchodilator inhalers where needed. This was inadequate to control viral induced asthma following winter infections where oral prednisone at 5 mg/day was required to reduce chronic wheezing and coughing to an acceptable level. The patient was administered 8 g/day of fungi-derived biologically-active emu oil in divided doses-4 g morning and night. Within 3 weeks all asthma symptoms reduced, and improvement continued following cessation of aerosol steroids.

After 2 months on the oil, the patient controlled all symptoms of asthma with 4 g/day of the oil and no other medication. In addition, the administration of the oil has reduced the need for LOSEC to be taken for the patient's gastric reflux.

6) Patient is a 62 year old female with a 51 year history of chronic asthma (Classified as chronic airways limited), which was controlled by 10-50 mg/day of oral prednisone, 900 mg/day of neulin, plus frequent use of ventolin/atrovent puffers and nebules was required to control chronic wheezing and coughing to an acceptable level. The patient was administered 6 ml of fungi-derived biologically-active emu oil in divided doses, 3 mL morning and night. The patient has been on this dose of oil for 11 months and this has virtually eliminated the wheezing noise, reduced the level of coughing, plus the level of prednisone has been reduced to 5 mg/day. Also use of puffers and nebules has been reduced. No longer needs to take Losec for gastric reflux. By increasing the emu oil to 9 mL/day, three 3 mL doses/day with a slight increase in prednisone to 10 mg/day any asthma attacks can be controlled (the oil synergistically increases activity of prednisone, as confirmed by a rat model). Her daily life style has been greatly improved since commencing use of this oil.

7) Patient is an Eurasian Male patient 23 years of age, diagnosed by colonoscopy, and is prescribed 40 mg prednisone daily reduced 5 mg every two weeks, 2 grams of mesalamine daily. 6 weeks later after blood results received, the patient is hospitalised and administered 7 days of hydrocortisone IV, lost 4 kg in weight, heads of hip bones began to die off as a resulting side effect of the medication. The patient is prescribed post-hospital medication of:
100 mg Imuran daily (intended four year treatment)
50 mg of prednisone daily (reducing 5 mg every two weeks).
The patient then began taking 5 ml of oil (batch 365) three times a day, and ceased all other medication within one month from starting on the oil. His medical problems continued to reduce in severity. Three months after starting on the oil the patient was instructed to take extract of oil (batch 365), two teaspoons daily, and has experienced no chronic symptoms in four months. The patient's health continues to improve (digestive system, stamina, fitness etc), with a weight gain of 5 kg. Cumulative C Reactive Protein reduced over a period of six months from 65.1 to 5.3 mg/L, Range (0.0-5.0) mg/L. The patient's results are summarised in Table 10 below.

CRP and ESR Results

TABLE 10

| Date | C Reactive Protein (High Sensitivity) Range (0.0-5.0) mg/L | ESR Range (0-20) mm/hr |
| --- | --- | --- |
| 07/08/03 | 65.1 | |
| 9/09/03 | 25.9 | |
| 21/10/03 | 33.5 | |
| 09/12/03 | 5.2 | 4 |
| 10/02/03 | 4.9 | 3 |
| 13/04/03 | 5.3 | 1 |

TABLE 11

| Chromatogram Number | Sample Code | Lipid Substrate | Fungal Mixture | Humidity | Temperature (° C.) | Time (days) |
| --- | --- | --- | --- | --- | --- | --- |
| 1 | A | emu | Rhodotorula mucilaginosa, Cryptococcus albidus, Trichosporon pullulans, Mucor spp, Epicoccum purpurescens, Rhizopus stolonifer, Penicillium chrysogenum, Nigrospora sphaerica, Chaetomium globosum, Alternaria alternata | High | 10-12 | 128 |
| 2 | C | emu | No fungi | High | 10-12 | 128 |
| 3 | Kalaya | emu | Rhodotorula mucilaginosa, Cryptococcus albidus, Trichosporon pullulans, Mucor spp, Epicoccum purpurescens, Rhizopus stolonifer, Penicillium chrysogenum, Nigrospora sphaerica, Chaetomium globosum | Medium | 10-15 | 128 |
| 4 | Type 2 | emu | Rhodotorula mucilaginosa, Cryptococcus albidus, Trichosporon pullulans, Mucor spp, Epicoccum purpurescens, Rhizopus stolonifer, Penicillium chrysogenum, Nigrospora sphaerica, Chaetomium globosum | High | 15-20 | 128 |
| 5 | E113 | emu | Mucor BB14 | High | 20 | 21 |
| 6 | E115 | emu | Mucor BB18 | High | 20 | 21 |
| 7 | E108 | emu | Penicillium chrysogenum | High | 20 | 21 |
| 8 | E109 | emu | Rhodotorula mucilaginosa | High | 20 | 21 |
| 9 | E110 | emu | Cryptococcus albidus | High | 20 | 21 |
| 10 | E111 | emu | Trichosporon pullulans | High | 20 | 21 |
| 11 | E112 | emu | Trichosporon pullulans, Rhodotorula mucilaginosa, Cryptococcus albidus | High | 20 | 21 |
| 12 | E116 | emu | Mucor Black | High | 20 | 21 |
| 13 | E117 | emu | All Mucor spp | High | 20 | 21 |
| 14 | E118 | emu | Trichosporon pullulans, Rhodotorula mucilaginosa, Cryptococcus albidus, Penicillium chrysogenum, Mucor BB14, Mucor BB16, Mucor BB18, Mucor Black | High | 20 | 21 |
| 15 | E104 | emu | Mucor BB14, Mucor BB16, Mucor BB18, Mucor Black | High | 20 | 21 |
| 16 | E119 | emu | Nil | High | 20 | 21 |
| 17 | L17 | lamb | Mucor Black | High | 20 | 24 |
| 18 | E90 | lamb | Penicillium chrysogenum, Mucor BB12, Mucor BB13, Mucor BB15, Mucor Black | Low to medium | 20 | 7 |
| 19 | E60 | macadamia | Cryptococcus albidus | Low | 20 | 14 |
| 20 | E80 | macadamia | Cryptococcus albidus | Low | 20 | 21 |
| 21 | TLWB1 | emu | Rhodotorula mucilaginosa, Cryptococcus albidus, Trichosporon pullulans, Mucor spp, Epicoccum purpurescens, Rhizopus stolonifer, Penicillium | Medium | 10-12 | 14 |

TABLE 11-continued

| Chromatogram Number | Sample Code | Lipid Substrate | Fungal Mixture | Humidity | Temperature (° C.) | Time (days) |
|---|---|---|---|---|---|---|
| | | | chrysogenum, Nigrospora sphaerica, Chaetomium globosum, Alternaria alternata | | | |
| 22 | TLOSTF | ostrich | Rhodotorula mucilaginosa, Cryptococcus albidus, Trichosporon pullulans, Mucor spp, Epicoccum purpurescens, Rhizopus stolonifer, Penicillium chrysogenum, Nigrospora sphaerica, Chaetomium globosum, Alternaria alternata | Medium | 10-12 | 14 |
| 23 | ZB2 | beef | Trichosporon pullulans, Rhodotorula mucilaginosa, Cryptococcus albidus, Penicillium chrysogenum, Mucor BB14, Mucor BB16, Mucor BB18, Mucor Black | Low | 20 | 63 |
| 24 | Type-B | emu | Rhodotorula mucilaginosa, Cryptococcus albidus, Trichosporon pullulans, Mucor spp, Epicoccum purpurescens, Rhizopus stolonifer, Penicillium chrysogenum, Nigrospora sphaerica, Chaetomium globosum, Alternaria alternata | Medium | 10-12 | 28 |
| 25 | M11 | Macadamia | Chaetomium sp | medium | 20 | 35 |
| 26 | M14 | Macadamia | Penicillium, Chaetomium, Absidia and Mucoraceous fungi, mixed through crushed nuts | medium | 20 | 35 |
| 27 | M14A | Macadamia | Absidia sp | medium | 20 | 35 |
| 28 | M15 | Macadamia | Penicillium, Chaetomium, Absidia and Mucoraceous fungi, fungi inoculated on surface of crushed nuts. | medium | 20 | 35 |
| 29 | M16 | Macadamia | Mucoraceous fungus | medium | 20 | 35 |
| 30 | M19 | Macadamia | Penicillium, Chaetomium, Absidia and mucoraceous fungi, fungi inoculated on surface of crushed nuts | high | 10 | 35 |
| 31 | M20 | Macadamia | Penicillium janczewski | medium | 20 | 28 |
| 32 | M21 | Macadamia | Penicillium sclerotiorum | medium | 20 | 28 |

That which is claimed:

1. A method of treating an inflammatory condition including musculo-skeletal disorder selected from the group consisting of arthritis, rheumatoid arthritis, osteoarthritis, and combinations thereof in a human or animal patient, said method comprising administration to the patient of an effective amount of a fungally-modified fat or oil and/or its extract containing newly synthesized biologically-active chemical compounds, produced according to a process comprising;
  a) isolating an endogenous fungus or an endogenous fungal mixture from a lipid substrate, wherein said endogenous fungus or said endogenous fungal mixture has enzymatic activity;
  b) sterilizing said lipid substrate, or sterilizing a second lipid substrate that is colonized by said endogenous fungus or said endogenous fungal mixture, to produce a sterilized lipid substrate;
  c) inoculating said sterilized lipid substrate with said endogenous fungus or said endogenous fungal mixture to produce an inoculated lipid substrate;
  d) incubating said inoculated lipid substrate for a period of between about 7-120 days at a temperature of between about 4-35° C., at a humidity of between about 75-100% to produce an incubated lipid substrate; and
  e) processing said incubated lipid substrate to obtain fungally-modified fat or oil and/or its extract containing newly synthesized biologically-active chemical coumpounds.

2. The method according to claim 1, wherein said administration is oral, transdermal or subcutaneous.

3. The method according to claim 1, wherein in step d) the period of incubation is between about 7 to 56 days, at a temperature of between about 5-20° C. and at a humidity of between about 80-100%.

4. The method according to claim 1, wherein said lipid substrate of step a) is animal-derived, and wherein said incubated lipid substrate is rendered in step e) to obtain said fungally-modified fat or oil.

5. The method according to claim 1, wherein the lipid substrate of step a) is plant or seed-derived, and wherein said fungally-modified fat or oil is obtained in step e) by cold pressing or solvent extraction of said incubated lipid substrate.

6. The method according to claim 1, wherein a concentrated extract of said fungally-modified fat or oil obtained in step e) is prepared by solvent extraction of said fungally-modified fat or oil using methanol at a low temperature.

* * * * *

UNITED STATES PATENT AND TRADEMARK OFFICE
CERTIFICATE OF CORRECTION

PATENT NO. : 8,629,181 B2  Page 1 of 1
APPLICATION NO. : 13/671401
DATED : January 14, 2014
INVENTOR(S) : Turner It is certified that error appears in the above-identified patent and that said Letters Patent is hereby corrected as shown below:

IN THE CLAIMS

Claim 1, Column 33, line 30, after "ing," insert -- a --.

Claim 1, Column 34, lines 30-31, delete "coumpounds" and insert -- compounds --.

Signed and Sealed this
Eighth Day of April, 2014

Michelle K. Lee
*Deputy Director of the United States Patent and Trademark Office*